United States Patent [19]
Gallup et al.

[11] Patent Number: 5,372,141
[45] Date of Patent: Dec. 13, 1994

[54] BODY COMPOSITION ANALYZER

[75] Inventors: David A. Gallup; Joseph M. Mercola, both of Schaumburg; William E. Shaw, Palatine, all of Ill.

[73] Assignee: Body Composition Analyzers, Inc., Schaumburg, Ill.

[21] Appl. No.: 907,028

[22] Filed: Jul. 1, 1992

[51] Int. Cl.$^5$ .............................................. A61B 5/05
[52] U.S. Cl. ................................................... 128/734
[58] Field of Search ............... 128/734, 741, 630, 632, 128/693, 774, 897–898, 903

[56] References Cited

U.S. PATENT DOCUMENTS

| | | | |
|---|---|---|---|
| 4,008,712 | 2/1977 | Nyboer | 128/734 |
| 4,895,163 | 1/1990 | Libke et al. | 128/734 |
| 4,911,175 | 3/1990 | Shizgal | 128/734 |
| 4,947,862 | 8/1990 | Kelly | 128/734 |
| 4,949,727 | 8/1990 | Yamazaki et al. | 128/734 |
| 5,003,984 | 4/1991 | Muraki et al. | 128/903 X |

Primary Examiner—Angela D. Sykes
Attorney, Agent, or Firm—McAndrews, Held & Malloy

[57] ABSTRACT

A body composition analyzer provides the resistive and reactive components of a body's measure impedance as well as body fat information and ideal weight information. The analyzer includes an analog circuit under the control of a microprocessor for providing signals to the microprocessor that are representative of the voltage across the network formed by the body and of the voltage across a reference network of known impedance that is connected in series with the body network. The microprocessor calculates the body networks impedance as a function of the ratio of the body network voltage and reference network voltage signals to provide extremely accurate results. The body composition analyzer is a hand-held unit that can transmit data to a peripheral device for recording via a wireless communication network. The analyzer is further programmable so that various algorithms and constants stored therein can be updated.

58 Claims, 16 Drawing Sheets

Fig. 3c
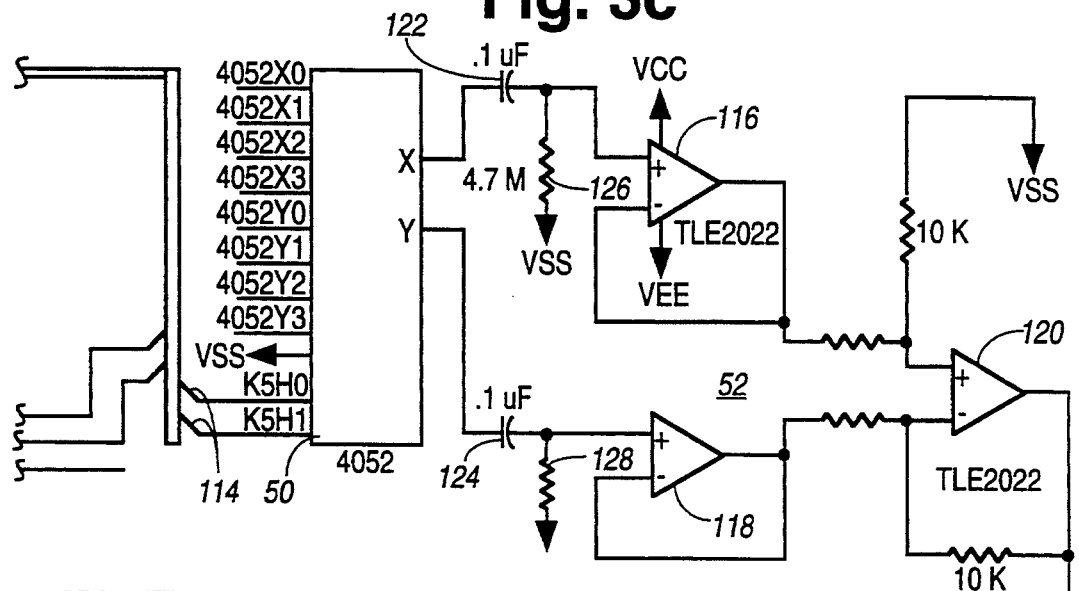
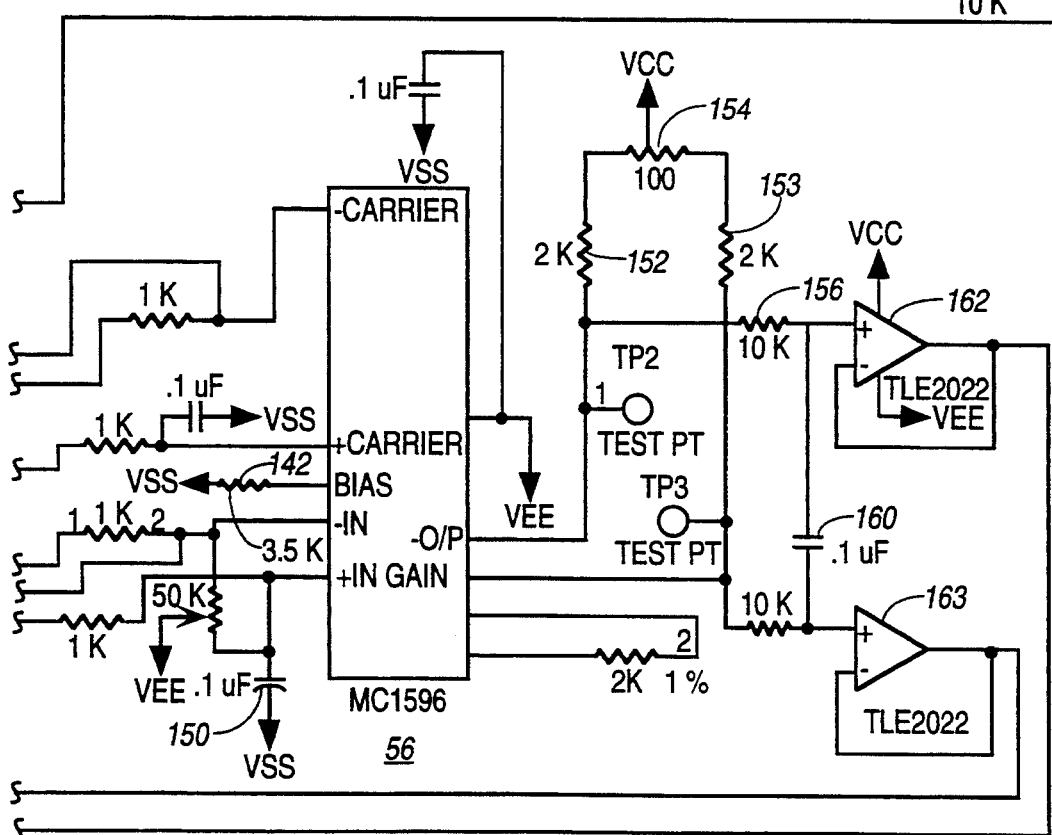
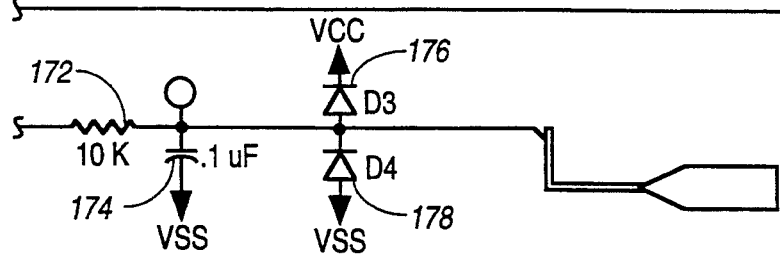

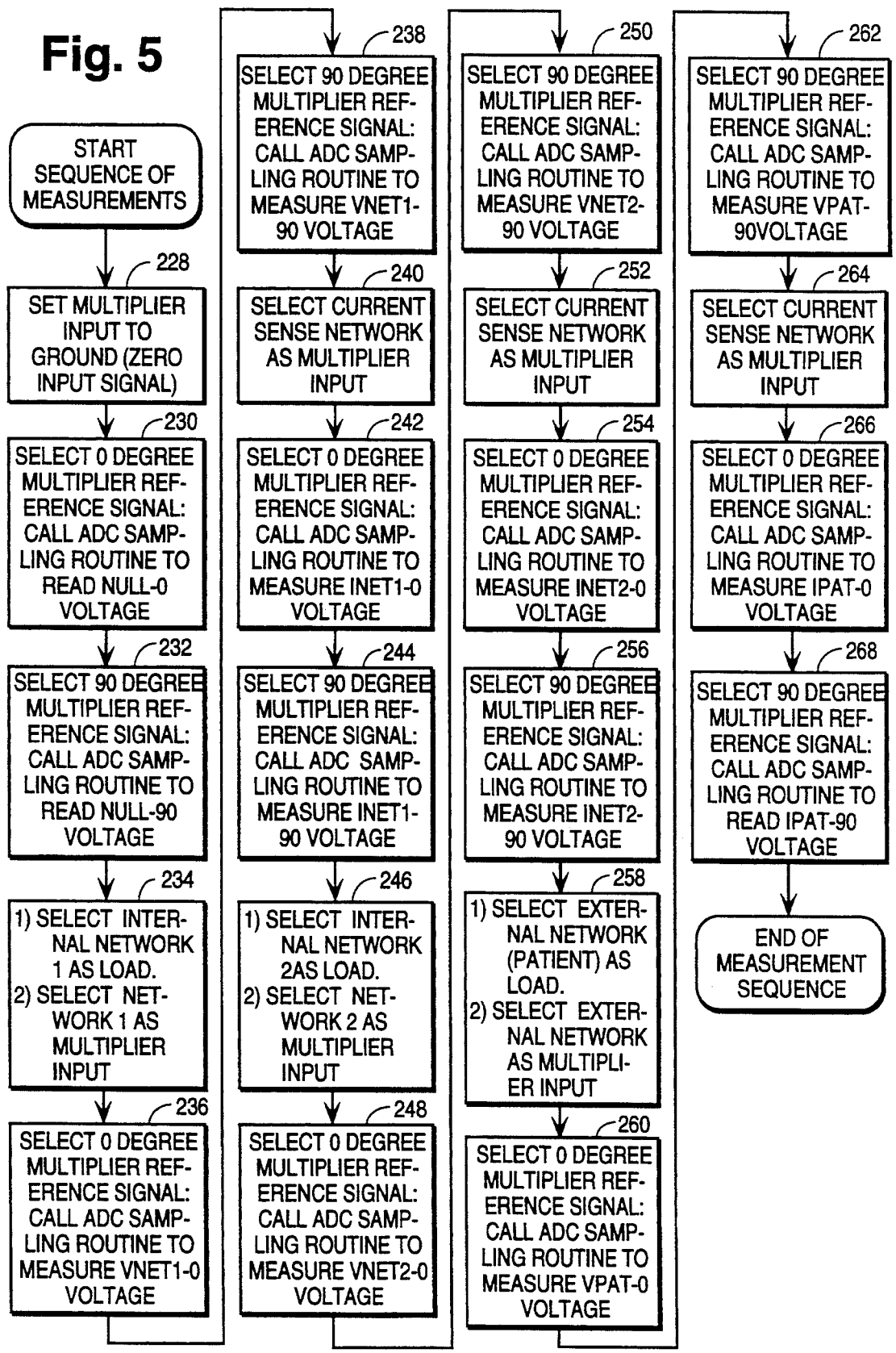

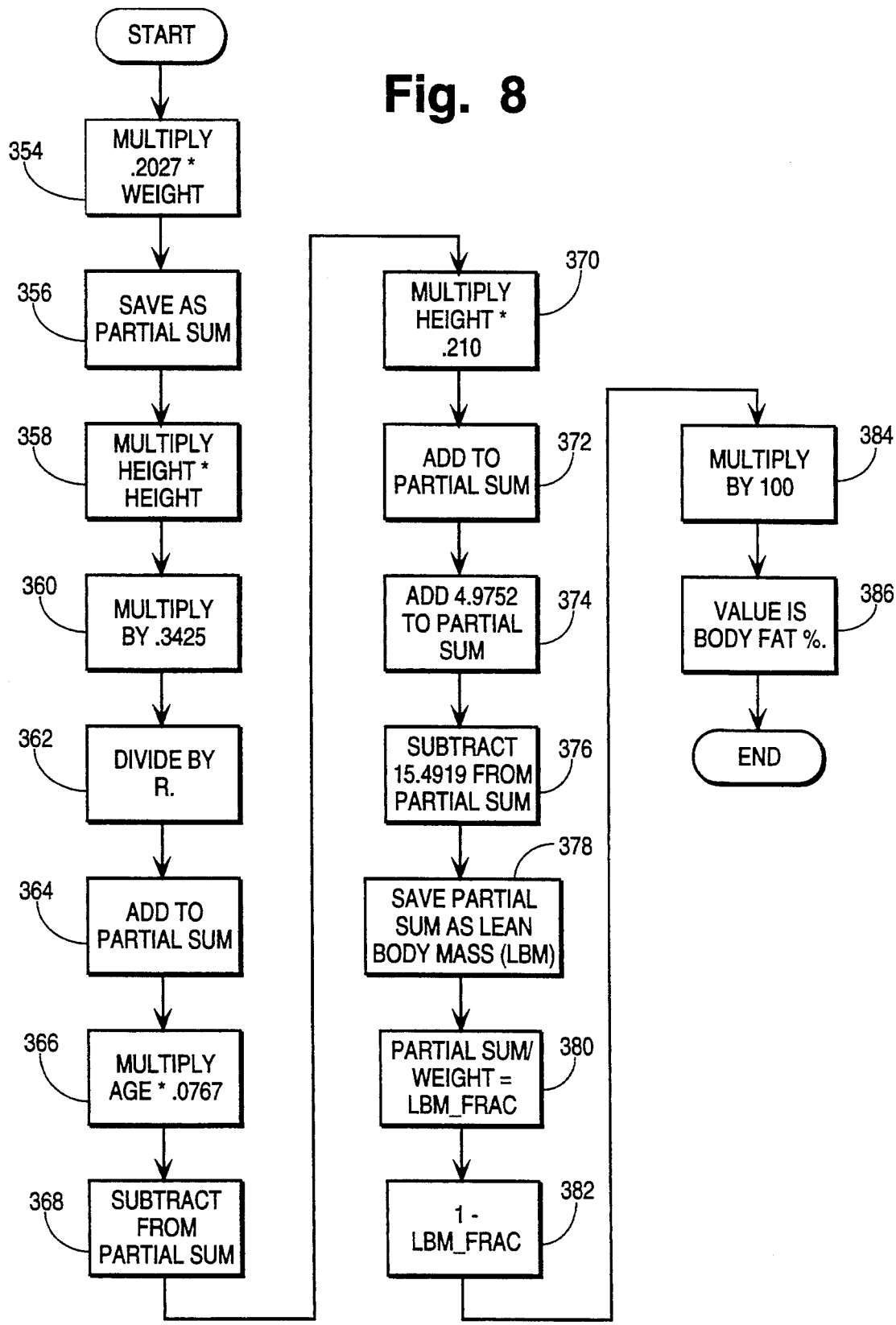

BODY COMPOSITION ANALYZER

TECHNICAL FIELD

The present invention relates to a body composition analyzer and more particularly to a body composition analyzer for determining resistance, reactance and a body fat percentage from a body's measured impedance. The analyzer utilizes a reference network in series with the network formed by a person's body wherein the unknown impedance of the body network is calculated from a ratio of a voltage sensed across the body network and voltage sensed across the reference network to provide extremely accurate measurements.

BACKGROUND OF THE INVENTION

Impedance meters are known for measuring the impedance of a person's body and from the impedance, the device determines a value representing the person's body fat. More particularly, one known device includes a table top analog impedance meter that displays a resistance value. A user can then enter the displayed resistance value into a personal computer that stores a body fat software algorithm. Another known device includes an integrated impedance meter and lap top computer that can be connected to a printer. A battery powered hand-held device is also known that includes a microprocessor control and provides body impedance measurements but does not provide the resistance and reactance components of the measured impedance. Each of the above known devices has one or more problems with: lack of accuracy; being hard to use due to size; being inflexible and non-updatable; and providing limited information to a user.

SUMMARY OF THE INVENTION

In accordance with the present invention, the disadvantages of prior body composition analyzers as discussed above have been overcome. The body composition analyzer of the present invention is a hand-held unit that provides highly accurate body impedance measurements including individual resistance and reactance measurements as well as body fat measurements and ideal weight information.

More particularly, the body composition analyzer of the present invention includes a number of electrodes attachable to the body of a person where the person's body forms a network of unknown impedance. A reference network of known impedance is coupled in series with the body network and a source of substantially constant peak-to-peak alternating current is coupled to the reference network as well as to at least one of the body electrodes. A voltage sensing circuit is coupled to a pair of the body electrodes as well as to the reference network to provide signals respectively representing the sensed voltage across the body network and the sensed voltage across the reference network. A digital processor is coupled to the voltage sensing circuit in order to calculate at least one value representing the unknown body impedance from the known impedance of the reference network and a ratio of the sensed voltage across the body network and the sensed voltage across the reference network. Because the unknown body impedance is calculated from a ratio of the sensed voltage across the body network and the sensed voltage across the reference network, the calculated impedance does not contain any phase angle error terms. Further, the calculated impedance is not dependent upon the current applied to the networks so that uncompensated changes in the magnitude of the current will not cause errors.

The body composition analyzer further includes means for multiplying each of the body voltage signal and the reference voltage signal by an in-phase signal and an out-of-phase signal that is shifted from the in-phase signal by ninety degrees. The multiplier thus provides an in-phase body network signal, an out-of-phase body network signal, an in-phase reference network signal and an out-of-phase reference network signal to the digital processor. The digital processor calculates the magnitude of the voltage across the body network from the in-phase and out-of-phase body network signals and further calculates the magnitude of the voltage across the reference network from the in-phase and out-of-phase reference network signals. The magnitude of the unknown body impedance is then calculated from the magnitude of the known impedance of the reference network times the ratio of the magnitude of the voltage across the body network to the magnitude of the voltage across the reference network. The digital processor further calculates the phase angle of the voltage across the body network from the in-phase and out-of-phase body network signals and calculates the phase angle of the voltage across the reference network from the in-phase and out-of-phase reference voltage signals. The phase angle of the unknown body impedance is then calculated from the ratio of the phase angle of the voltage across the body network and the phase angle of the voltage across the reference network.

The body composition analyzer of the present invention determines a value representative of the person's body fat from the person's calculated body resistance and from information entered via a keyboard, the information including the weight, height and age of the person whose body composition is being analyzed. A number of body fat algorithms and/or a number of constants used in one or more body fat algorithms are stored in the unit wherein the digital processor selects the particular body fat algorithm and/or constants to be used in the algorithm according to information input to the analyzer such as the person's gender, age and/or ethnicity, i.e. nationality and/or race.

The body composition analyzer also calculates a value representing the person's ideal weight in accordance with a predetermined body fat percentage value selected by a user from a set of stored values, each of which represents the body fat percentage value of a person of particular fitness. For example, the analyzer stores typical body fat percentage values for a relatively active male and female, for male and female athletes, and for male and female top athletes. The user can also enter a body fat percentage value to be used in the ideal weight calculations. The body fat algorithms and constants used in the algorithms are stored in a nonvolatile programmable memory such as in EEPROM to allow the body composition analyzer to be updated so that the most current body fat equations developed by scientists and researchers can be used. Further, the structure of the software is such that the digital processor means stores a number of arithmetic operation software subroutines separately from the body fat algorithm that calls the routines so that when the body fat algorithm is updated the mathematical operation routines do not have to be updated. The updating of the body composition analyzer is thus easily accomplished.

The body composition analyzer of the present invention further includes means for determining conditions that indicate the possibility of inaccurate impedance measurements and means for displaying a warning to the user upon detection of such a condition. More particularly, the body composition analyzer includes a load network having a measurable impedance. The load network can be coupled in series with the reference network and to the voltage sensing circuit to provide a signal representative of the sensed voltage across the load network and a signal representative of the sensed voltage across the reference network with the load network connected to the reference network. The digital processor calculates at least one value representative of the impedance of the load network from the known reference network impedance and a ratio of the sensed voltage across the load network to the sensed voltage across the reference network. The calculated impedance is then compared to a predetermined value to determine whether it is within limits or not. Two load networks, the impedance for both of which are calculated may be used to determine a condition indicating the possibility of an inaccurate impedance measurement wherein one of the networks has low resistive and high reactive components whereas the other network has high resistive and low reactive components. The body composition analyzer also detects whether a lead fault has occurred, whether the person is over or under hydrated, and whether the battery powering the unit is low since all of these conditions can possibly result in inaccurate impedance measurements.

Further in accordance with the present invention, the body composition analyzer includes an infrared transmitter to provide wireless communication with a P.C. and/or printer capable of receiving such communications so that a print out of the reactance, resistance, body fat percentage and ideal weight values as well as other information relating to the person may be printed.

These and other objects, advantages and novel features of the present invention as well as details of an illustrative embodiment thereof will be more fully understood from the following description and the drawings.

BRIEF DESCRIPTION OF THE DRAWING

FIGS. 3A-3C form a schematic diagram of the body composition analyzer illustrated in FIG. 1;

FIG. 5 is a flow chart illustrating a measure routine;

FIG. 8 is a flow chart illustrating a body fat algorithm;

DESCRIPTION OF THE PREFERRED EMBODIMENT

Figure 1:
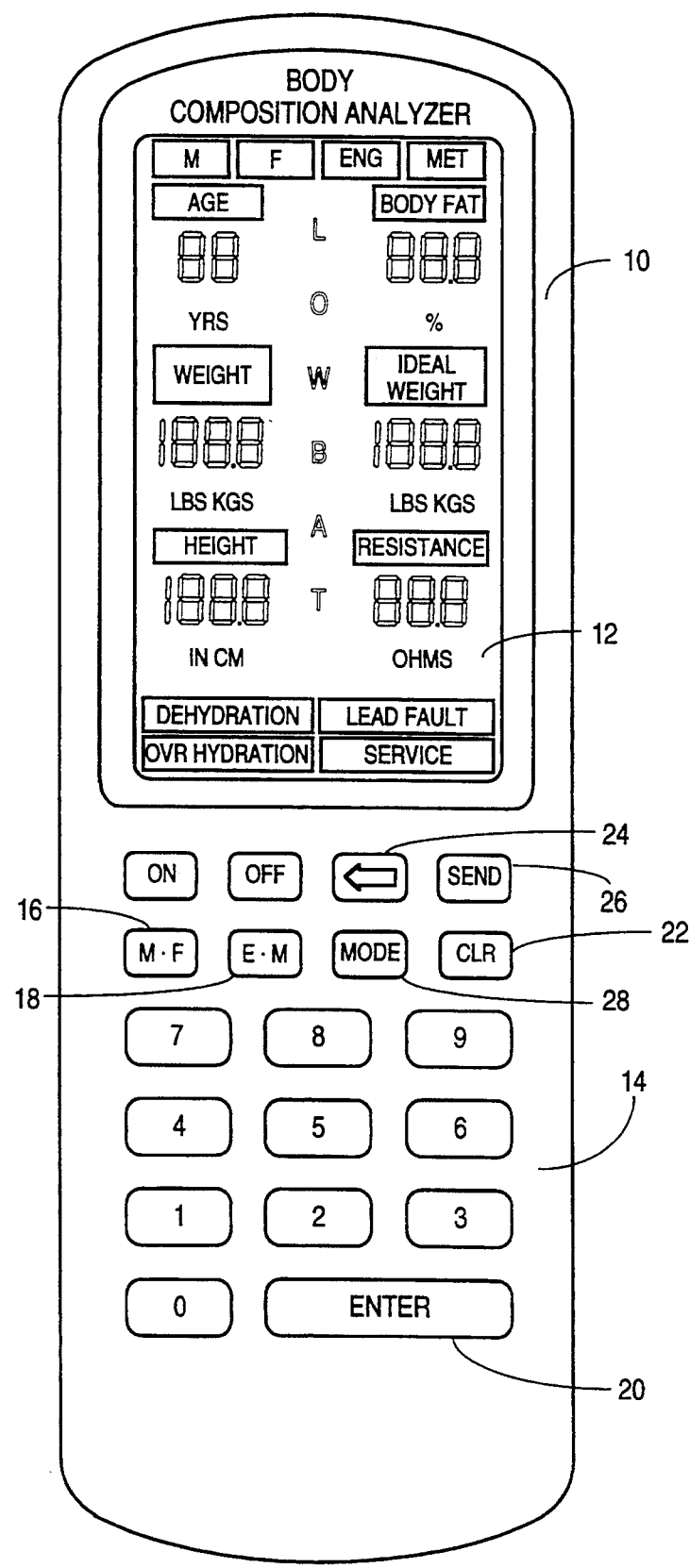
FIG. 1 is a perspective view of the body composition analyzer of the present invention.
Figure 2:
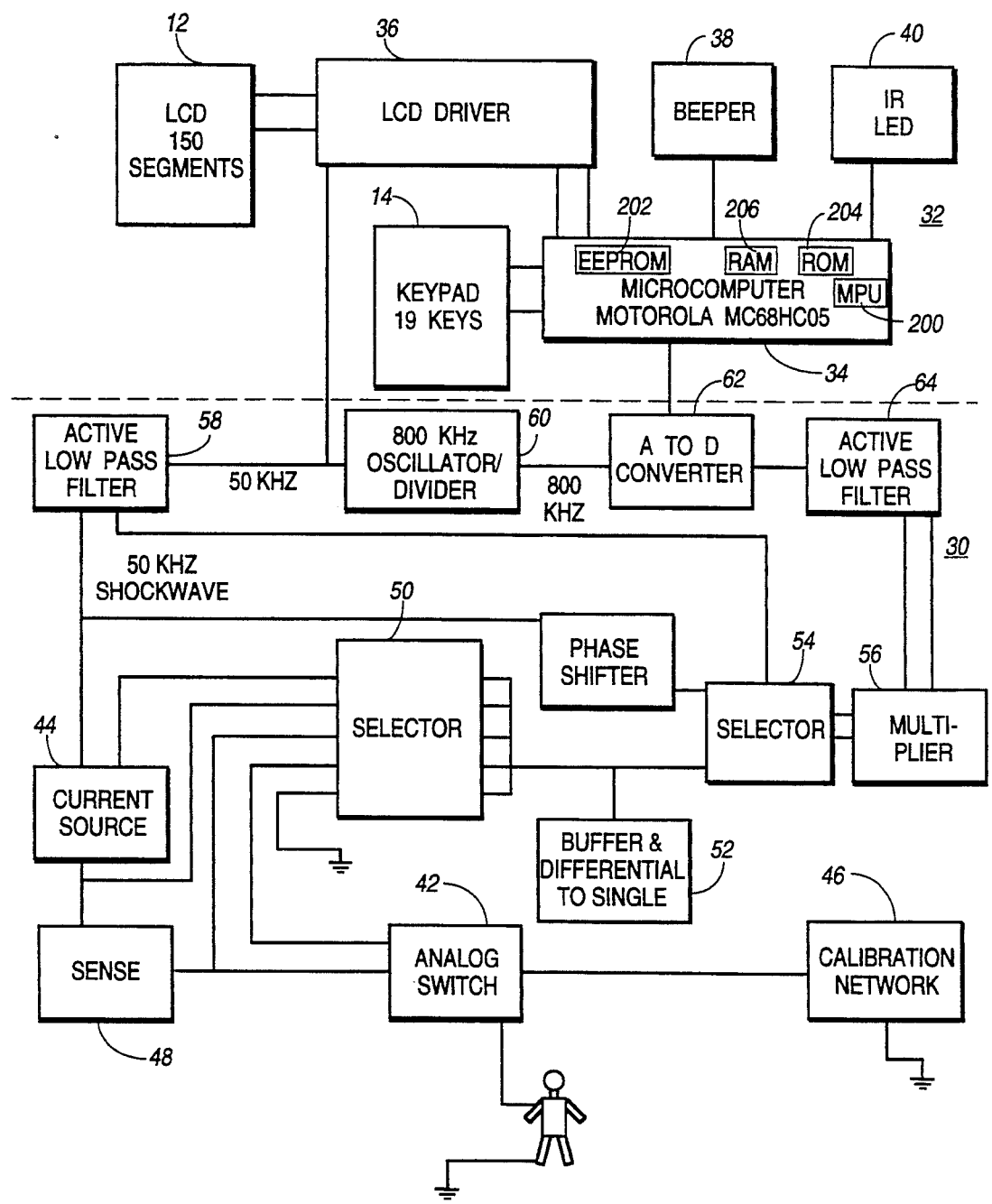
FIG. 2 is a block diagram of the body composition analyzer shown in FIG. 1.

The body composition analyzer in accordance with the present invention as shown in FIGS. 1 and 2 is a hand-held unit 10 having a display 12 and a keyboard 14 for entering data. The analyzer unit 10 is attached to the body of a person whose composition is to be measured using a tetrapolar electrode arrangement wherein the body represents an "electrical" body network, the impedance of which is to be determined. The tetrapolar arrangement includes a first distal electrode that is adhered to the anterior surface of the person's foot in the area of the second metatarsal-phalangeal joint. A second distal electrode is adhered to the dorsal surface of the person's hand, in the area of the third metacarpal phalangeal joint. A first proximal electrode is adhered to the anterior surface of the person's ankle, midway between the malleoli and a second proximal electrode is adhered to the dorsal surface of the wrist, just distal to and midway between the radial and ulnar styloid processes.

After the electrodes are in place, in an operational measurement mode, information regarding the person's sex, age, weight and height are entered utilizing the display 12 and keyboard 14. More particularly, after power to the unit 10 is turned on the unit 10 enters a Enter Gender and Units data mode. In this mode, either a "M" character or "F" character will be blinking on the display 12 depending on the default setting for the gender display segment. By pressing a M/F key 16, the character that had not been blinking starts to blink while the other character stops blinking. Similarly, in this state, either the English, "ENG", or metric, "MET", portion of the display 12 will blink depending on the default setting of the unit's display segment. By actuating an E/M key 18 the units segment of the display that had been blinking will stop and the other units display segment will start to blink. When an enter key 20 is pressed, the analyzer unit 10 stores the gender of the person represented by the blinking gender character and also stores the units of measurement selected by a user as represented by the blinking units display segment. The analyzer unit 10 then enters an Enter Age Data mode. In this mode an age segment of the display blinks to prompt a user to enter a two-digit number representing the user's age via the keyboard 14. If the clear button 22 is pressed once, the number depicted in the age segment of the display goes to zero. By actuating the clear key 22 twice in a row, the unit 10 proceeds back to the mode for entering the gender and units of measurement as discussed above. However, by pressing the enter key, the age data entered via the keyboard 14 and displayed in the age display segment is stored for later calculations. The unit then proceeds to a Weight Data Entry mode in which a weight segment on the display is blinked so as to prompt the user to enter the person's weight. In the Weight Data Entry mode, if the clear key 22 is pressed once, the number displayed in the weight segment is reset to zero. By pressing the clear key 22 twice in a row, all of the numbers on the display are returned to zero and the mode of the unit returns to the Enter Gender and Units Data mode. However, by pressing the enter key 20, the unit 10 proceeds to a Height Data Entry mode. In this mode the user is prompted to enter height information by the blinking height segment of the display. In the Height Data Entry mode, if the clear key 22 is pressed once, the height field is reset to zero; whereas pressing the clear key twice in a row resets the unit to the Enter Gender and Units Data mode. It is noted that if a left arrow key 24 is pressed during any of the entry modes, the unit 10 proceeds to the immediately preceding data entry mode.

After entering the person's height and actuating the enter key 20, the system automatically enters a measurement operation mode to measure the person's impedance and in particular the resistance and reactance components thereof. In this mode the person's percentage of body fat and ideal weight are also calculated. After performing the various measurements and computations, the unit 10 automatically and simultaneously displays the person's body fat percentage, ideal weight and resistance on the display 12 in an associated portion of the display. Once this information is displayed, if the clear key 22 is actuated, the unit returns to the Enter gender and units data mode. However, if the enter key is pressed, the unit automatically repeats the various measurements and displays updated information to the user. By pressing the left arrow key 24, the unit returns back to the height data entry mode to allow the user to enter a different height value. If power to the unit is turned off, actuation of the left arrow key 24 upon subsequent power up causes the unit to retrieve from memory the data stored for the last measurement, the data being displayed on the display 12. If a send key 26 is actuated, a message is transmitted via an infrared LED to a personal computer or printer capable of receiving such a transmission so that a data record may be stored and/or printed, the record representing the person's entered and measured/calculated data. A mode key 28 is provided to allow the user to enter various configuration menus.

In one configuration mode, the user can set the time, date and year so that measurements are time stamped. A second mode allows the user to select ideal body fat percentages for use in the ideal weight calculations. More particularly, the unit 10 stores a body fat percentage table with values representing the ideal body fat of a world class male athlete and a world class female athlete in an elite mode; the body fat percentages for a male and a female having a very good level of fitness such as a high school athlete in a competitive mode; and the body fat percentages for a male and female in normal physical condition, i.e. relatively active, in a standard mode. In a user mode, the user can enter a target body fat percentage which is stored for use in the ideal weight calculations as discussed below. In a third configuration mode the unit can be configured to display various default values upon start up. For example, the default setting for gender may be set to the male gender display segment so that this display segment blinks upon the powering up of the unit 10. A default setting may also be selected for the units of measurement display segment. In this mode, the body composition analyzer unit 10 may also be set to operate in a research mode wherein the measured teacrance of a person is displayed as well as the person's measured body resistance. In the research mode, the display 12 will display the resistance and reactance values in an alternating manner. Finally, in a printer selection mode, the user may select a particular receiver/printer format utilizing the keyboard 14 and display 12.

As shown in FIG. 2, the body composition analyzer 10 includes an analog portion 30 and a digital portion 32 contained within the housing of the unit 10. The digital portion of the analyzer unit 10 includes a microcomputer 34 such as a Motorola MC68 HC05. The microcomputer 34 is coupled to the keyboard 14 to receive inputs therefrom. The microcomputer 34 is also coupled to the display 12 through a display driver 36 wherein the display 12 may be formed of a 150 segment liquid crystal display. A beeper 38 controlled by the microcomputer 34 provides audible messages to a user to confirm data entry and to indicate errors. An infrared LED 40 is controlled by the microcomputer 34 as discussed below so as to transmit information to a printer such as a Hewlett Packard, HP82240B printer. The infrared LED 40 may also be controlled to send information to a label printer, personal computer or the like which are capable of receiving infrared transmissions. This enables a body composition data to be stored via the personal computer or a hard copy or label containing the data to be obtained from the printer.

The microcomputer 34 also controls the sequence of various measurements performed by the analog portion 30 of the analyzer unit 10. More particularly, the microcomputer 34 controls an analog switch 42 to direct current from a current source 44 to various load networks the impedance of which is to be determined. The current source 44 provides a 50 khz substantially constant peak-to-peak sine wave directed by the analog switch 42 to either the distal electrodes coupled to the body network or to a calibration network 46. The calibration network 46, as discussed in detail below actually consists of two calibration networks, the first having low resistance and high reactance components of impedance and the second network having high resistance and low reactance components of impedance. The resistance and reactance components of the first and second calibration networks are measured and compared to predetermined values to enable diagnostics to be performed for the system in order to detect system errors.

A sense network 48 having a known impedance is placed in series with the body network whose impedance is unknown and to be measured. The sense network is also coupled in series with the calibration networks 46. The sense network 48 is utilized so that the impedance of the network, i.e. body network or either of the calibration networks, to be measured can be calculated as a ratio of the voltage sensed across the network to be measured and the voltage sensed across the sense network as described in detail below. Because the measurements are calculated utilizing ratios, the measurements are not dependant upon current and in particular upon uncompensated changes in the magnitude of the current. Nor do the results include any phase angle error terms.

The microcontroller 34 controls a selector switch 50 to pick up 1) the voltage across the body network of the person; 2) the voltage across the sense network 48; 3) the voltage across the first calibration network; or 4) the voltage across the second calibration network so as to couple the selected voltage to a buffer and differential amplifier stage 52. The microcontroller 34 also controls a further selector switch 54 to select which signals to apply to the input of a multiplier 56. More particularly, the multiplier 56 multiplies each voltage selected by the selector 50 and output from the buffer and differential amplifier stage by an in-phase signal and an out-of-phase signal, the latter of which is shifted from the former by ninety degrees. The in-phase and out-of-phase signals are coupled to the multiplier 56 through the selector switch 54 from a low pass filter 58 that is coupled to the output of an oscillator 60. The oscillator 60 and low pass filter 58 form a portion of a signal generator as discussed in detail below with respect to FIG. 3A. The output of the multiplier 56 is coupled to an analog to digital converter 62 through a low pass filter 64.

The microcomputer 34 is responsive to the digital representations of the products of the sensed voltage across each of the networks (the body network, the sense network and the first and second calibration networks) and the in-phase and out-of phase signals to calculate the impedance of the body network as well as the impedance of each of the calibration networks. The impedance calculations are based upon phasor arithmetic. More particularly, the magnitude of the phasor representing the voltage across a particular network, $V_x$ can be expressed as $$|V_x| = \sqrt{(V_{x0})^2 + (V_{x90})^2} \qquad \text{Eq. (1)}$$

where $V_{x0}$ represents the voltage of the particular network multiplied by the in-phase signal and where $V_{x90}$ represents the voltage across the particular network times the out-of-phase signal. Similarly, the phase angle $\Theta_{vx}$ of the phasor representing the voltage across a particular network can be expressed as $$\Theta_{vx} = Tan^{-1}(V_{x90}/V_{x0}). \qquad \text{Eq. (2)}$$

Similarly, the magnitude of the phasor representing the voltage across the sense network can be expressed as $$|V_s| = \sqrt{(v_{s0})^2 + (v_{x90})^2} \qquad \text{Eq. (3)}$$

and the phase angle of the phasor representing the voltage across the sense network can be expressed as $$\Theta_{vs} = Tan^{-1}(V_{x90}/V_s)). \qquad \text{Eq. (4)}$$

Since the current through the sense network is the same as the current applied to the network the impedance of which is to be measured, the unknown impedance, $Z_x$, of the network can be expressed as follows:

$$Z_x = \frac{|V_x| \angle \Theta_{vx}}{|V_s| \angle \Theta_{vs}} Z_s \angle \Theta_{zs} \qquad \text{Eq. (5)}$$

where $Z_s$ is the known impedance of the sense network and $\Theta_{zs}$ represents the known phase difference between the 50 khz signal applied to the particular network and the in-phase signal. Therefore the magnitude of the impedance $Z_x$ can be expressed as $$|Z_z| = |V_x Z_x V_s| \qquad \text{Eq. (6)}$$

and the phase angle of the unknown impedance can be expressed as $$\Theta_{zx} = \Theta_{vx} - \Theta_{vs} + \Theta_{zs}. \qquad \text{Eq. (7)}$$

Further, the resistance of the network X is defined as $$|Z_x|Cos(\Theta_{zx}); \qquad \text{Eq. (8)}$$

whereas the reactance component of the impedance is as follows:

$$|Z_x|sin(\Theta_{zx}). \qquad \text{Eq. (9)}$$

Because the unknown impedance of the body network is calculated in accordance with the ratio set out in equation (5), it is not dependant upon current so that uncompensated changes in the magnitude of the current will not result in errors. Further, the impedance calculation does not include any phase angle error term.

Figure 3A:
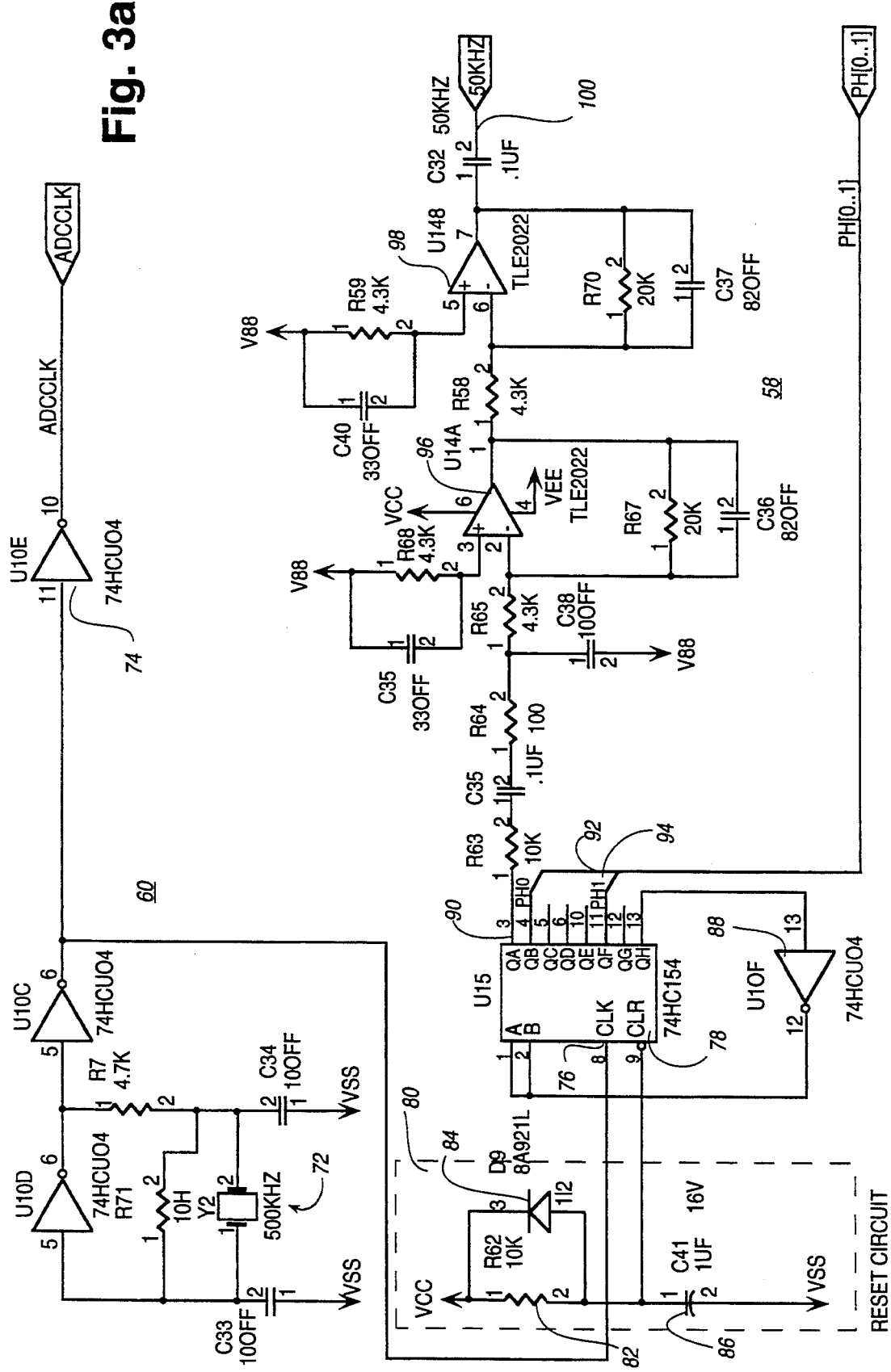
Figure 3B:
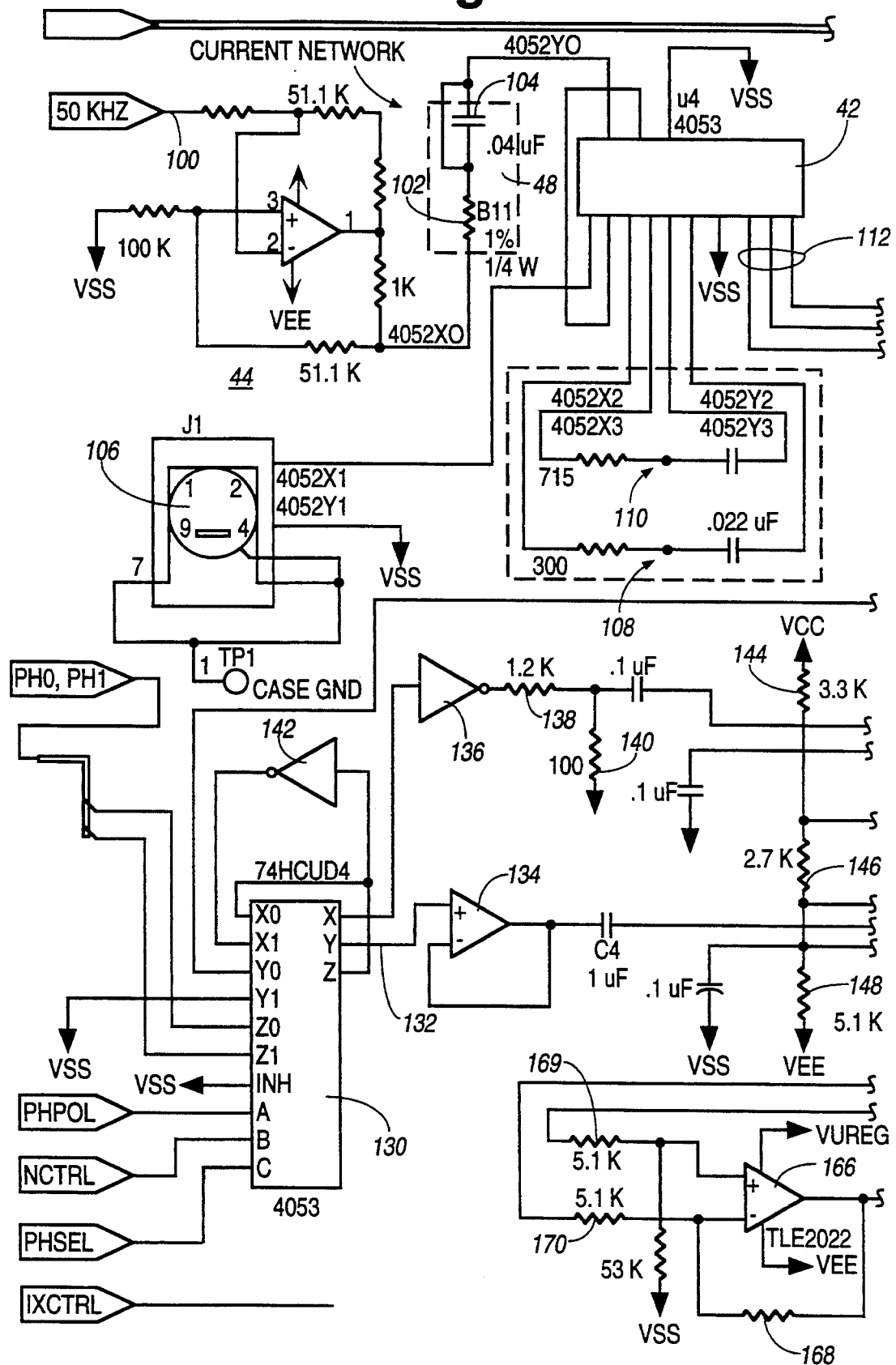

Details of the analog portion 30 of the body composition analyzer unit 10 will now be described with reference to FIGS. 3A–C. A signal generator shown in FIG. 3A generates a nominal two-volt peak-to-peak 50 kilohertz sine wave that is applied to the current source 44; two 50 khz squarewaves that are phase shifted by ninety degrees, respectively representing the in-phase and out-of-phase multiplier signals PH0 and PH1; and an 800 hkz square wave at digital logic levels for the analog to digital converter 62. The signal generator includes an 800 khz oscillator 60, a 50 khz square wave generator 70 and the low pass filter 58. More particularly, the oscillator 60 includes an 800 khz ceramic resonator 72 that controls the frequency of the oscillator 60. The output of the oscillator 60 is the 800 khz square wave that is applied to the analog to digital converter 62 through an inverter 74 so as to provide an external clocking signal to the analog to digital converter 62. The output of the oscillator 60 is also coupled to the clock input 76 of an 8 bit parallel output shift register 78. A reset circuit 80 formed of a 10 kΩ resistor 82 connected to a 1 microfarad capacitor 86 with a diode 84 connected across the resistor is coupled to the clear input of the shift register 78. On power up, the reset circuit 80 generates a reset signal to the shift register 78 so that all of the 8 bits of the shift register are set to zero. The output of the shift register is fed to the input of an inverter 88 the output of which is connected back to the input of the shift register 78 so that the contents of the shift register are toggled every 8 clock cycles. After every 16 clock cycles, the entire shift register returns to its original state. Since the shift register is reset to zero on power up, the wave form repeats every 16 clock cycles. Thus the output frequency of the wave form on a line 90 is 50 khz and is used to generate the 50 khz signal applied to the respective body network, sense network and calibration networks. Because the entire waveform repeats every 16 clock cycles and at any one time the shift register holds exactly one half of the waveform, each output line or tap of the shift register represents a phase shift of 22.5° and the phase difference between any two taps that are spaced four taps apart are out-of-phase by 90 degrees. Therefore, the outputs of the shift register on respective lines 92 and 94 represent the in phase signal PH0 and the out-of-phase signal PH1 for the multiplier. Further, the 22.5° phase difference between PH0 and the 50 khz signal on line 90 represents $\Theta_{zs}$. The 50 hkz square wave output from the shift register 78 on line 90 is applied to the low pass filter 58. The low pass filter 58 includes a pair of operational amplifiers 96 and 98 with feed back networks so as to cause the cut off frequency of the filter to be approximately 60 khz. A cut off frequency of approximately 60 khz is sufficiently low so that for practical purposes only the 50 khz fundamental of the square wave passes through the filter.

The 50 khz, two-volt peak-to-peak sine wave output from the low pass filter 58 on a line 100 is applied to the input of a constant current source 44 so as to provide a nominal 500 UA current that is applied to the sense network 48 as well as to the series connected patient network and first and second calibration networks. The sense network 48 may include a resistive component provided by a resistor 102 and a reactive component provided by a capacitor 104 connected in series with the resistor 102. However, it has been found that utilizing the resistor 102 alone to form the sense network 48 provides very accurate results without the need to use the capacitor 104. The main requirement of the sense network 48 is that the impedance thereof Z, be known precisely. Where the sense network is formed by the resistor 102 alone, $Z_s$ is equal to the value of the resistor 102.

The analog switch 42, which may be a CMOS 4053 type of analog switch, is coupled between the sense network 48 and the body electrodes 106 as well as a first calibration network 108 and a second calibration network 110. The first calibration network 108 has a low resistive component and high reactive component of impedance; whereas the second calibration network has a high resistive component and a low reactive component of impedance. The switch 42 is responsive to the control signals applied thereto from the microcomputer 34 on lines 112 to connect the sense network in series with either the body network coupled thereto by the electrodes 106, the first calibration network 108 or the second calibration network 110. The voltage selector switch 50 is a CMOS 4052 type of analog switch that is a dual four to one multiplexer/demultiplexer. The voltage across the sense network is applied to the selector switch 50 via the lines labeled 4052X0 and 4052Y0. The voltage across the body network as sensed by the two proximal body electrodes is applied to the selector switch 50 via lines 4052X1 and 4052Y1. The voltage across the first calibration network 108 is applied to the voltage selector switch 50 via lines 4052X2 and 4052Y2; whereas the voltage across the second calibration network is applied to the voltage selector switch 50 via lines 4052X3 and 4052Y3. The voltage selector switch 50 is responsive to control signals on lines 114 from the microcomputer 34 to select one of the four voltage inputs to the differential amplifier circuit 52. The differential amplifier circuit 52 includes a pair of operational amplifiers 116 and 118 configured as voltage followers and an operational amplifier 120 that is configured as a differential amplifier having a gain of unity. The signals coupled to the voltage followers 116 and 118 from the voltage selector switch 50 are coupled thereto by 0.1 microfarad capacitors 122 and 124 so as to block any residual DC offset that might be present if the current source 44 is not completely symmetrical about zero current. The voltage follower inputs to the operational amplifier 120 are utilized because of their inherently high input impedance. Further, the value of the coupling capacitors 122 and 124 is chosen to provide a relatively small reactive load, the voltage drop thereacross being very small so that it does not adversely affect the measurements. The resistors 126 and 128 bleed off any input offset current that might be present from the operational amplifier 120. The output of the operational amplifier 120 represents the difference between the voltages applied to the input thereof.

The output of the operational amplifier 120 is applied to the input of a multiplier control analog switch 130. The multiplier control switch 130 is a CMOS 4053 type of control switch consisting of three individual two to one demultiplexers, each of which has its own control signal that originates from the microcomputer 34. More particularly, a control signal NCTRL from the microprocessor 34 is applied to the multiplier control switch 130 during calibration so that the voltage signal of a particular network input to the switch 130 is grounded and the output adjusted to zero volts. As discussed below, during actual measurements of the voltage across the body network, the products of the in-phase and out-of-phase signals times the null voltage is stored and subtracted from all other voltage measurements to correct for drift in the analog circuitry. The output of the network voltage/null voltage control portion of the switch 130 on a line 132 is coupled to the input of an operational amplifier 134 configured as a voltage follower. The voltage follower 134 drives the relatively low impedance of the multiplier input and prevents the voltage drop across the switch 130 from skewing the final results. In response to a phase control signal PHSEL from the microprocessor 34, the switch 130 selects either the in-phase signal PH0 or the out-of-phase signal PH1 from the signal generator for multiplication by a selected network voltage signal. The in-phase signal corresponds to multiplying by the cosine function whereas the out of-phase signal corresponds to multiplying by the sine function. The in-phase or out-of-phase signal output from the switch 130 is applied to an inverter 136 whose output is scaled down by a pair of resistors 138 and 140 so as to provide an input signal that is within the range of the multiplier input. The switch 130 is responsive to a polarity control signal PHPOL applied thereto to select an additional inverter 142 if necessary. The inverter 142 may be required because some phasor combinations can result in negative values for one or both of the multiplication products unless an additional 180° is added to the reference phase term. This is required because the product must be within the zero to five volts range of the analog to digital converter 62.

The signal representing the network voltage output from the differential amplifier block 52 and coupled through the switch 130 to the voltage follower 134 is applied to the multiplier 56 so as to be multiplied by either the in-phase or out-of phase signals coupled to the multiplier 56 by the switch 130, inverter 136 and associated circuitry. More particularly, the multiplication function is handled by a balanced modulator integrated circuit of the type MC1496 or MC1596 as shown. With the MC1596, the in-phase and out-of-phase signals drive the carrier transistors of the device as current switches. The differential signal from the voltage across a particular network drives the inputs of the device. With regard to the MC1596, the output collectors should be at least 2.0 volts higher than the base voltage for the upper pair; the base voltage for the upper pair should be at least 2.7 volts greater than the base voltage for the lower pair and the base voltage for the lower pair should be at least 2.7 volts greater than the base voltage for the current source. The current level of the MC1596 is set by a resistor 142. The resistors 144, 146 and 148 form a voltage divider network that sets the bias voltage levels of the device. Further, a potentiometer 150 is used for null adjustments to balance the current when no input is applied. The resistors 152, 153 and a potentiometer 154 form the load resistor for the multiplier 56. The output voltage is taken differentially across the resistors 152 and 153 wherein the signal voltage is doubled. These resistors also control the signal gain for the multiplier. The potentiometer 154 is used as an offset and zero adjustment so that any differences in the resistors can be nulled. It is noted, that the potentiometer 154 may be removed and the offset compensated for in software if desired. A pair of resistors 156 and 158 and a capacitor 160 coupled therebetween form a low pass filter to remove high frequency components from the signal. The voltage across the capacitor 160 represents the DC component of the multiplication product. A pair of voltage followers 162 and 163 drive a differential amplifier 166. The gain of the differential amplifier 166 is set by the ratio of the feedback resistor 168 to the input resistors 169 and 170. The output of the differential amplifier is applied to a low pass filter formed of a resistor 172 and capacitor 174 to remove any residual alternating current from the signal. The output of the low pass filter is thereafter applied to the analog to digital converter 62 wherein the diodes 176 and 178 limit the input voltage to the analog to digital converter 162. The microcomputer 34 then samples the analog to digital converter 162 to obtain the various in phase and out-of-phase voltage values applied thereto as discussed below.

The microcomputer 34 includes a microprocessor 200 that operates in accordance with software stored in an EEPROM 202 and a ROM 204 while using a RAM 206 as a scratchpad memory during the various impedance, body fat and ideal weight calculations. Software that is to be updated, including the body fat and ideal weight algorithms as well as data tables storing constants and the like for use in the body fat and ideal weight algorithms are stored in the EEPOM; whereas software and fixed information may be stored in the ROM. Because the EEPROM is programmable, the body fat and ideal weight algorithms as well as the data tables stored therein are easily updatable so that the body composition analyzer unit 10 can employ the most current medical research information available. This is very important since new information relating to the accuracy of the algorithms is continually being developed by researchers in the field. The structure of the software according to which the microcomputer 34 operates is such as to aid in the ease with which the body fat and ideal weight algorithms and data tables can be updated. More particularly, individual subroutines for performing the various mathematical operations of the algorithms are stored independently of the main body fat and ideal weight algorithms that call these routines. This allows the main algorithms to be relatively short and easily replaceable without requiring the replacement of the mathematical operation subroutines called by the main algorithms.

Figure 4:
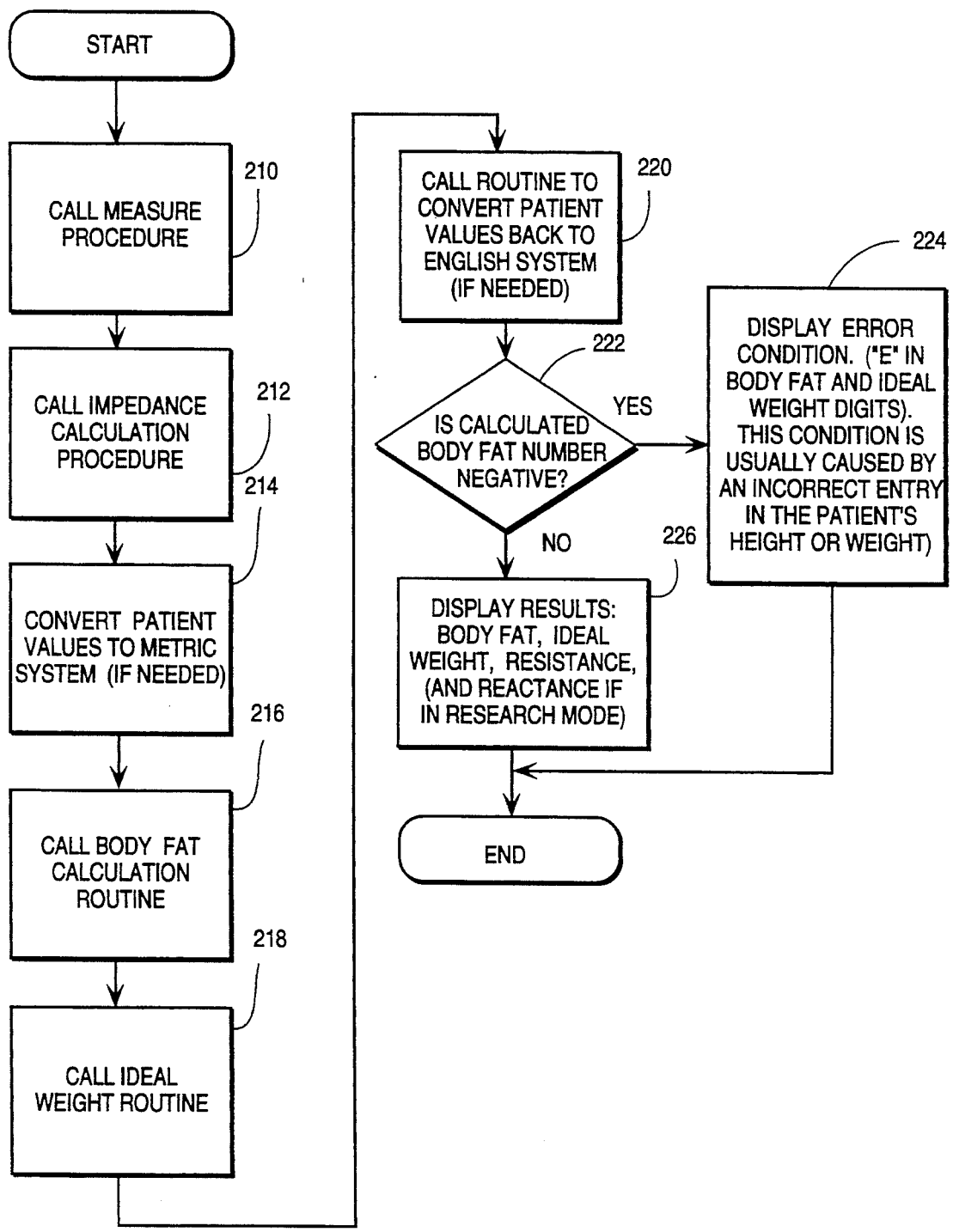
FIG. 4 is a flow chart illustrating a main processing routine of the body composition analyzer.
Figure 9:
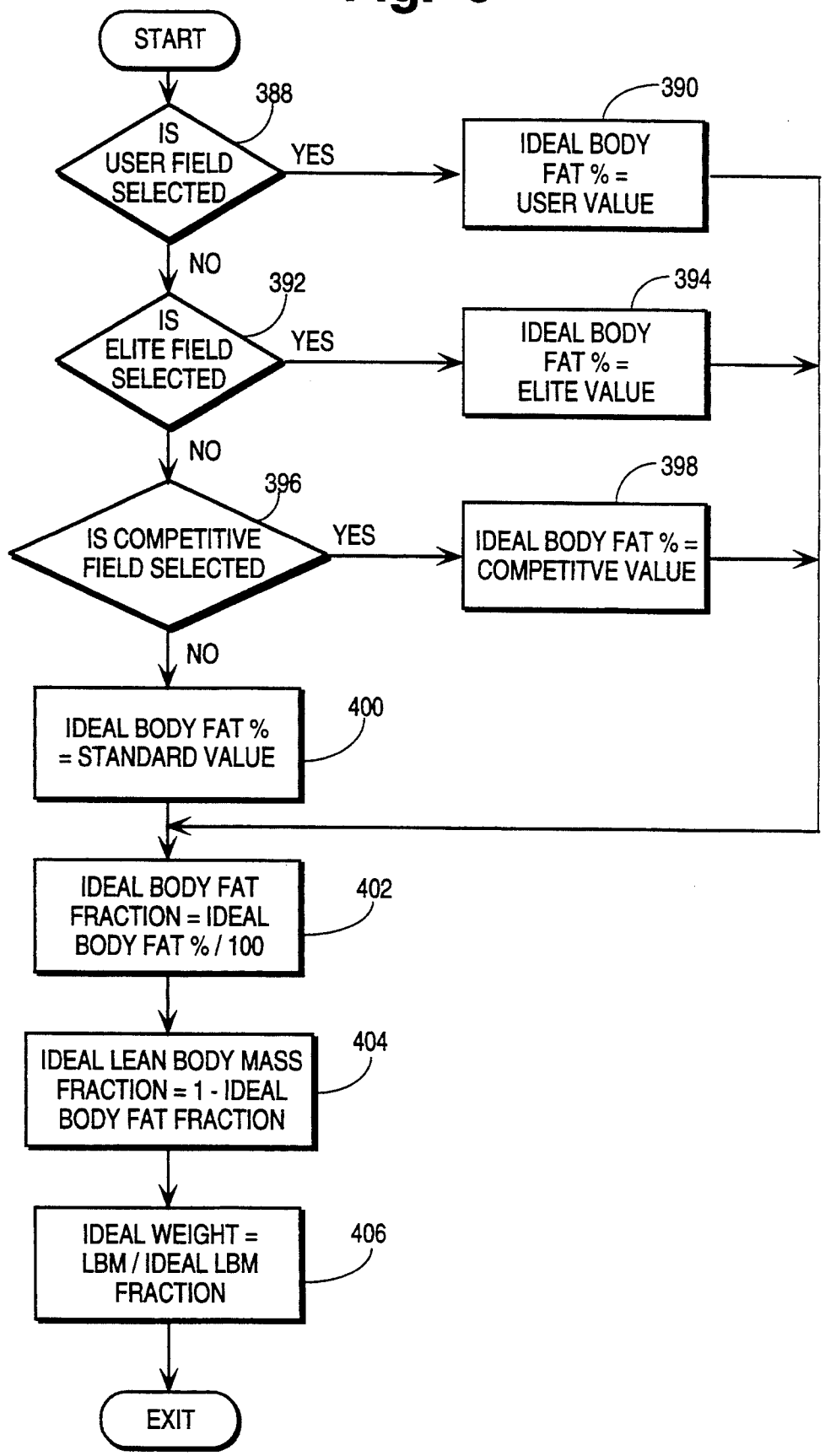
FIG. 9 is a flow chart illustrating an ideal weight calculation routine.

The general sequence of operations of the analyzer unit 10 when determining body composition is illustrated in the Main routine depicted in FIG. 4. More particularly, upon entering the Main operation routine from the data entry mode as discussed above, the microprocessor 200 at a block 210 calls a measure routine depicted in the flow chart of FIG. 5 so as to control the various selector switches depicted in FIG. 2 so that the required sequence of voltage measurements can be obtained. After all of the voltage measurement data is obtained by the microprocessor 200, the microprocessor proceeds to block 212 to call an impedance calculation routine depicted in FIGS. 7A-B in order to compute the impedance and in particular the resistance and reactance components of the body network as a ratio of the sensed voltage across the body network and the sensed voltage across the sense network 48. The impedance calculation routine further computes the resistance and reactance components of the impedance of the first and second calibration networks to determine if any conditions exist that may result in inaccurate body impedance measurements. Thereafter, the microprocessor 200 converts the calculated impedance values for the person to metric units if needed and proceeds to block 216. The microprocessor 200 then selects the appropriate body fat algorithms and/or constants for use therein based on the gender, age and/or ethnicity or race of the person as input via the keyboard 14 and implements the selected algorithm at block 216. After performing the body fat calculations at block 216 the microprocessor 200 proceeds to block 218 to implement an ideal weight algorithm as depicted in FIG. 9. Thereafter, at a block 220 the microprocessor 200 converts the calculated values to Metric units from English units if needed. At block 222, the microprocessor 200 determines whether the calculated body fat value is negative or not. If the calculated body fat value is negative, the microprocessor proceeds to block 224 to provide an error condition via the display and/or beeper. It is noted that this condition is typically caused by an incorrect entry in the patient's height or weight so that once the user is apprised of the error, the person's weight and height can be re-entered via the keyboard and the impedance, body fat and ideal weight calculations re-performed. If the calculated body fat number is not negative, the microprocessor 200 proceeds from block 222 to block 226 to display the results, i.e. the person's calculated body fat, ideal weight, resistance and if the unit is being operated in a research mode, the person's reactance component of impedance. The microprocessor 200 operates in accordance with the flow chart depicted in FIG. 5 to control the analog portion 30 of the circuitry and to sample the requisite voltages for the impedance calculations. More particularly, upon entering this routine, the microprocessor at a block 228 sets the input of the multiplier 56 to ground. Thereafter, at a block 230 the microprocessor 200 selects the in-phase multiplier signal PH0 via the selector 54 and calls an analog to digital converter sampling routine shown in FIG. 6 to read the in-phase voltage of the system. Thereafter, at block 232 the microprocessor 200 selects the out-of-phase multiplier signal PH1 via the selector switch 54 and calls the analog to digital converter sampling routine to read the null, out-of-phase voltage of the system. The null voltages sampled at blocks 230 and 232 are subtracted from all of the other measurements to correct for any drift in the analog circuitry as discussed below. At a block 234, the microprocessor 200 then selects the first calibration network 108 as the load placed in series with the sense network 48 via the switch 42. At block 234 the microprocessor 200 also selects the voltage across the first calibration network 108 via the switch 50 to be applied to the multiplier 56. At block 236, the microprocessor 200 selects the in-phase multiplier signal PH0 via the selector switch 54 and calls the analog to digital sampling routine to sample the product of the in-phase signal PH0 and the voltage across the first calibration network. Thereafter, at block 238 the microprocessor 200 selects, via the selector 54, the out-of-phase signal PH1 and calls the analog to digital converter sampling routine to sample the product of the out-of-phase signal and the voltage across the first calibration network. At block 240 the microprocessor selects the sense network 48 via the selector 50 as an input to the multiplier 56. Thereafter, at block 242 the microprocessor 200 selects the in-phase multiplier PH0 and calls the analog to digital converter sampling routine to sample the product of the in-phase signal and the voltage across the sense network with the first calibration network 108 connected in series therewith. Thereafter, at block 244, the microprocessor 200 selects the out-of-phase signal and calls the analog to digital converter sampling routine to sample the out-of-phase signal and voltage across the sense network with the first calibration network 108 connected in series therewith. At block 246, the microprocessor 200 selects the second calibration network 110 as the load via the switch 42 and selects via the switch 50 the voltage across the second calibration network as an input to the multiplier 56. At block 248 the microprocessor 200 then selects the in-phase signal via the switch 54 and calls the analog to digital converter sampling routine to sample the product of the voltage across the second calibration network 110 and the in-phase signal. Thereafter, at a block 250 the microprocessor selects the out-of-phase signal and calls the analog to digital converter sampling routine to sample the product of the voltage across the second calibration network and the out-of-phase signal. At block 252 the microprocessor 200 selects the sense network 48 as an input to the multiplier 56 via the switch 54 and proceeds to block 254 to select the in-phase multiplier. At block 254 the microprocessor also calls the analog to digital converter sampling routine to sample the product of the voltage across the sense network and the in-phase signal with the second calibration network as the load. Thereafter, the microprocessor 200 proceeds to block 256 to select the out-of-phase signal PH1 and calls the analog to digital converter sampling routine to sample the product of the in-phase signal and the voltage across the sense network with the second calibration circuit connected in series therewith. At a block 258 the microprocessor 200 selects the body network as the load via the switch 42 and further selects the voltage across the body network via the switch 50 as an input to the multiplier 56. At block 260, the microprocessor 10 selects the in phase multiplier signal and calls the analog to digital converter sampling routine to sample the product of the voltage across the patient and the in-phase signal. Thereafter, the microprocessor at block 262 selects the out-of-phase signal PH1 and calls the analog to digital converter sampling routine to measure the product of the voltage across the body network and the out-of-phase signal. At block 264 the microprocessor 200 again selects the sense network 48 as an input to the multiplier 56 via the selector 54 and at block 266 selects the in phase signal as an input to the multiplier 56. At block 266 the microprocessor 200 calls the analog to digital converter sampling routine to sample the product of the in-phase signal and the voltage across the sense network with the body network connected in series therewith. At block 268 the microprocessor 200 then selects the out-of-phase signal PH1 and calls the analog to digital converter sampling routine to sample the product of the out-of-phase signal and the voltage across the sense network with the body network connected in series therewith.

Figure 6A:
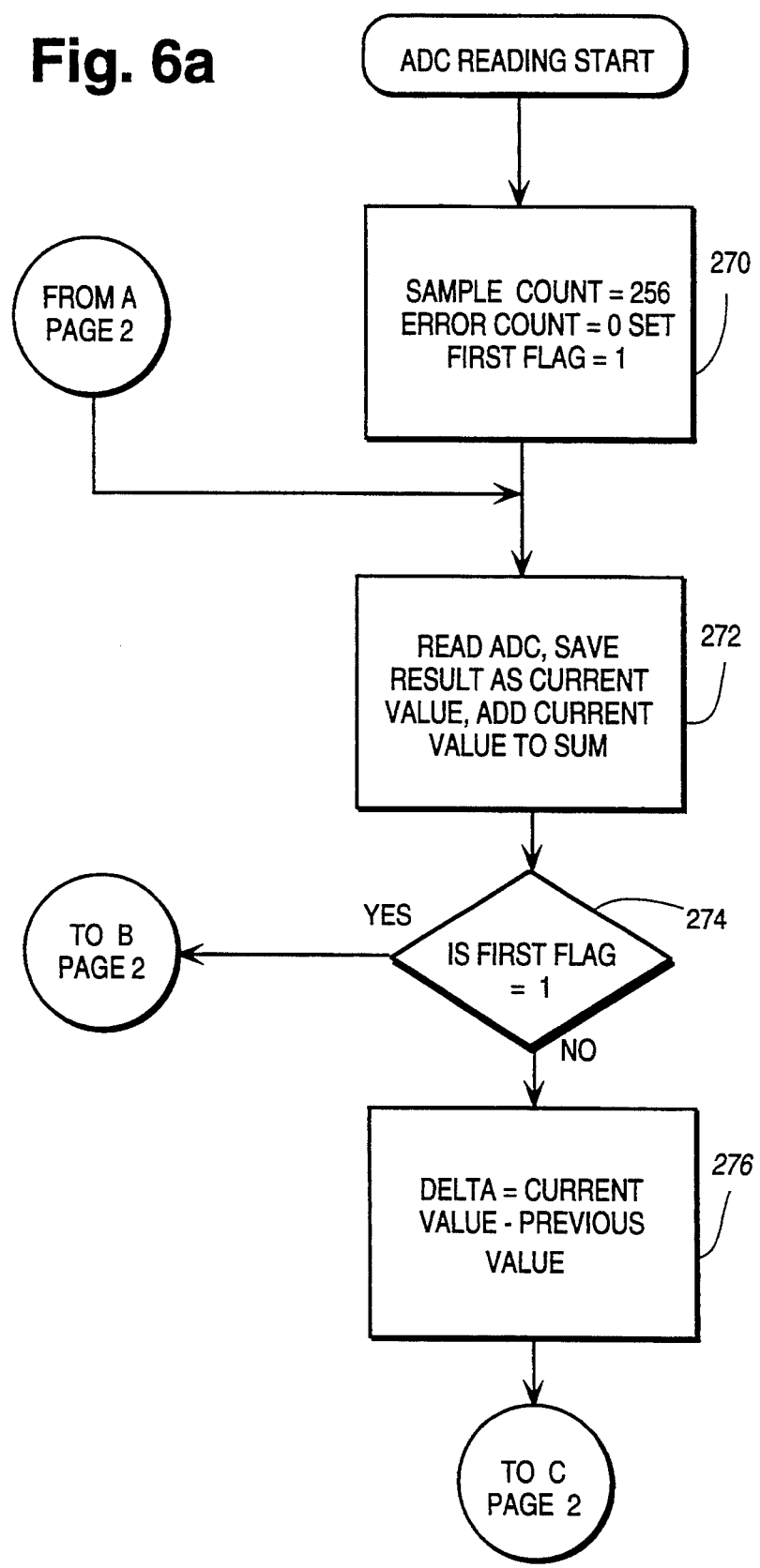
FIGS. 6A-6B form a flow chart illustrating an analog to digital converter sampling routine.
Figure 6B:
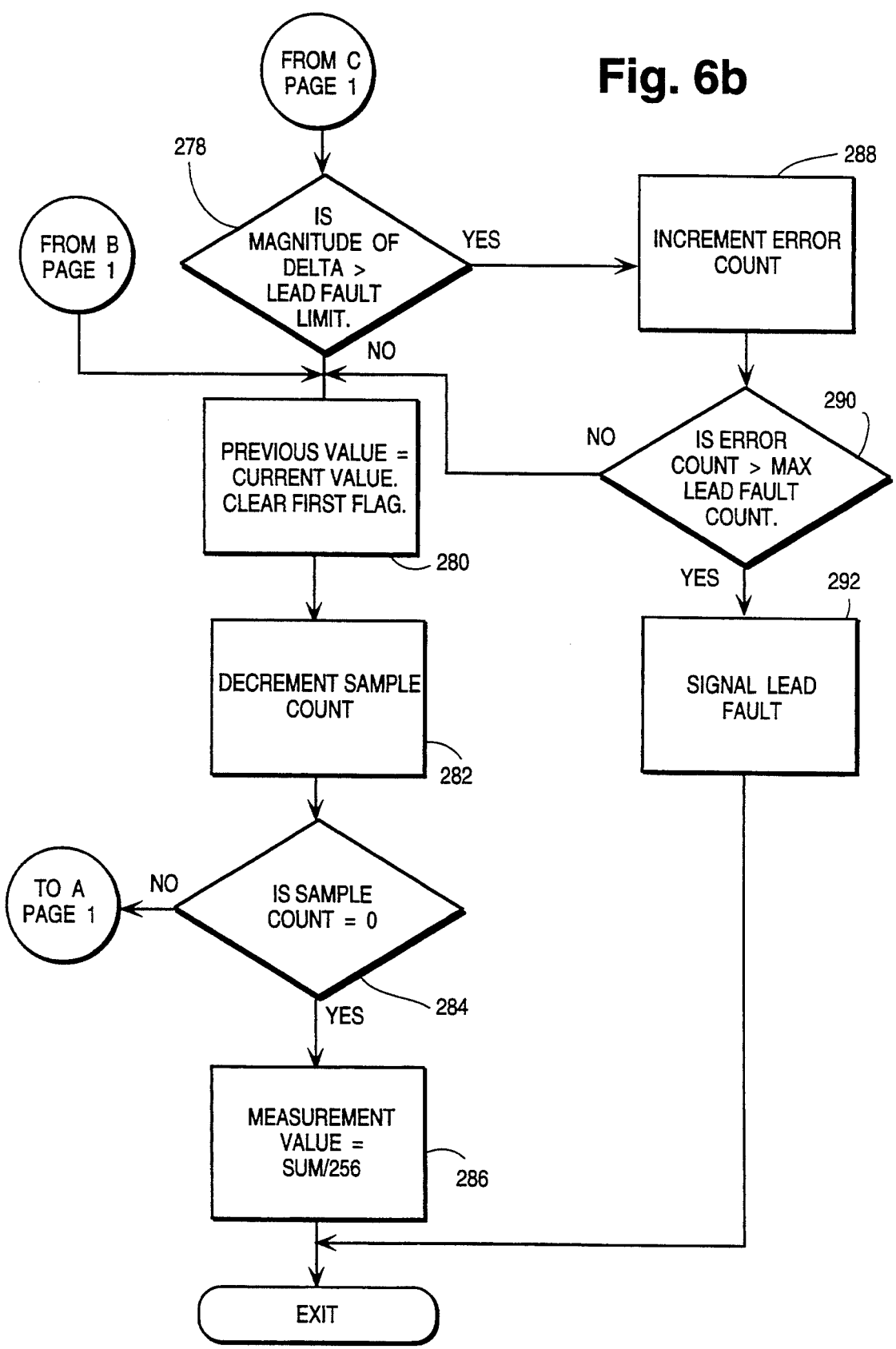

The analog to digital converter sampling routine is depicted in FIGS. 6A-B. Upon entering the routine, the microprocessor 200 at a block 270 sets the sample count equal to 256, the error count equal to 0 and a first flag to 1. At a block 272 the microprocessor 200 then reads the analog to digital converter 62 and saves the result of the read operation as the current value. At block 272 the microprocessor 200 also adds the current value to a sum for averaging. At block 274 the microprocessor then determines whether the first flag is set to 1 such that this is the first pass through the routine and if so, the microprocessor proceeds to block 280 to set the previous value equal to the current value. At block 280 the microprocessor 200 also clears the first flag. Thereafter, at a block 282, the microprocessor decrements the sample count by one and at block 284 determines whether the sample count has been decremented to zero or not. If not, the microprocessor proceeds back to block 272 to again read the analog to digital converter; to save the result as the current value; and to add the current value to the sum. Upon the second pass through the routine, the microprocessor 200 determines at block 274 that the first flag is not set equal to zero and proceeds to block 276 to determine a delta value which is equal to the current value saved at block 272 minus the previous value saved at block 280. The microprocessor 200 then proceeds to block 278 to determine whether the magnitude of delta calculated at block 276 is greater than a lead fault limit value. If so, the microprocessor proceeds to block 288 to increment an error counter. From block 288 the microprocessor proceeds to block 290 to determine whether the error count is greater than a maximum lead fault count and if so, the microprocessor proceeds to block 292 to signal a lead fault so that the unit can apprise the user of the condition via either the display 12 or the beeper 38. When the microprocessor 200 determines at block 284 that the analog to digital converter 62 has been sampled 256 times, the microprocessor proceeds to block 286 to determine the average value sampled from the analog to digital converter by dividing the sum by 256. Thereafter, the microprocessor 200 exits the analog to digital converter sampling routine.

Figure 7A:
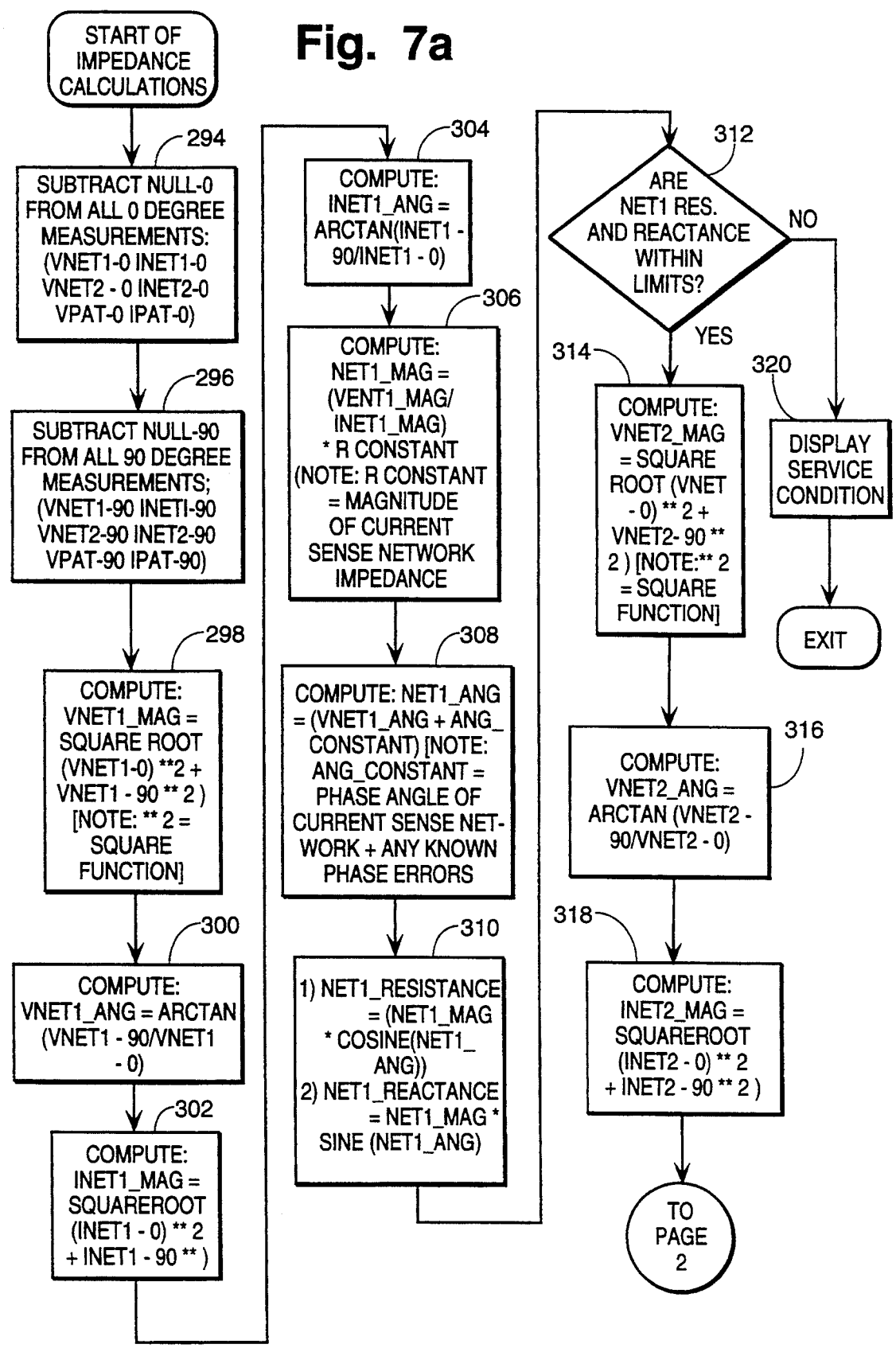
FIG. 7A-7B form a flow chart illustrating an impedance calculating routine.
Figure 7B:
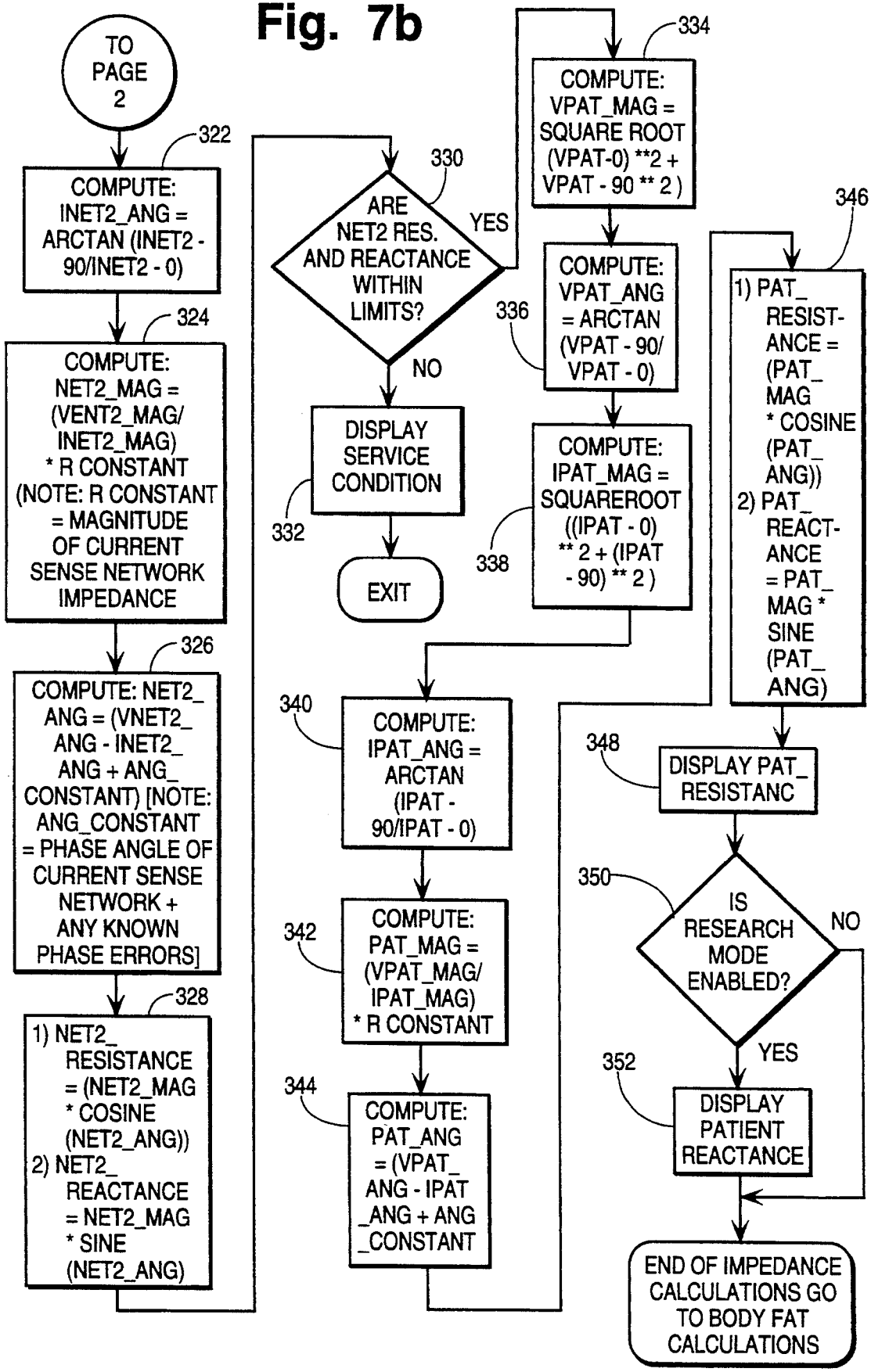

The microprocessor 200 calculates the impedance and more particularly the resistance and reactance of each of the calibration networks 108 and 110 and of the body network respectively as a ratio of the sensed voltage across the particular network and the voltage across the sense network 48 in accordance with the flow charts depicted in FIGS. 7A-B. More particularly, at block 294 the microprocessor 200 subtracts the null in-phase voltage determined at block 230 from each of the in-phase measurements for the first calibration network 108, the second calibration network 110, the body network and the sense network obtained at respective blocks 236, 248, 260, 242, 254 and 266. Thereafter, at a block 296 the microprocessor 200 subtracts the null out of-phase voltage read at block 232 from each of the out-of-phase voltage products of the first network 108, second network 110, the body network and the sense network obtained at blocks 238, 250, 262, 244, 256 and 268. The microprocessor 200 then computes at a block 298 the magnitude of the voltage across the first calibration network in accordance with equation (1). Further, at block 300 the microprocessor 200 calculates the phase angle of the voltage across the first calibration network in accordance with equation (2). At respective blocks 302 and 304 the microprocessor 200 calculates the magnitude and phase angle of the voltage across the sense network from the measurements taken with the first calibration network as the load in accordance with respective equations 3 and 4. Thereafter, at a block 306 the microprocessor 200 calculates the magnitude of the impedance of the first calibration network in accordance with equation (6) and at block 308 the microprocessor calculates the phase angle of the impedance of the first calibration network in accordance with equation (7).

At block 310, the microprocessor 200 determines the resistance of the first calibration network by multiplying the magnitude of the first calibration network's impedance by the cosine of the phase angle of the first calibration network's impedance in accordance with equation (8). Similarly, the reactance of the first calibration network is calculated by multiplying the magnitude of the first network's impedance by the sine of the phase angle of the first calibration network's impedance in accordance with equation (9). At block 312 the microprocessor 200 determines whether the resistance and reactance values calculated at block 310 for the first calibration network are within limits and if not, the microprocessor 200 proceeds to block 320 to control the display 12 to display a service condition. If the resistance and reactance values of the first calibration network are within limits the microprocessor proceeds to block 324.

At block 324 the microprocessor calculates the magnitude of the voltage across the second calibration network and at block 316 calculates the phase angle of the voltage across the second calibration network in accordance with respective equations (1) and (2). Thereafter, at blocks 318 and 322 the microprocessor 200 calculates the magnitude and the phase angle of the sense network 48 in accordance with equations (3) and (4) and with the measurements obtained at blocks 254 and 256. At block 324 the microprocessor utilizes the values calculated at blocks 314, 316, 318 and 322 to calculate the magnitude of the impedance of the second calibration network in accordance with equation (6) and at block 326 the microprocessor 200 calculates the phase angle of the second calibration network in accordance with equation (7). At block 328 the microprocessor 200 thereafter computes the resistance and reactive components of the second calibration network from the magnitude and phase angle of the impedance of the second calibration network. The microprocessor then determines at block 330 whether the resistance and reactance values calculated for the second calibration network are within limits and if not, the microprocessor proceeds to block 322 to control the display 12 to display a service condition. If, however, the resistance and reactance values calculated for the second calibration network are within limits, the microprocessor 200 proceeds to block 334.

At block 334 the microprocessor 200 computes the magnitude of the voltage across the body network in accordance with equation (1) and at block 336 the microprocessor 200 computes the phase angle of the voltage across the body network in accordance with equation (2). Thereafter, at respective blocks 338 and 340 the microprocessor 200 determines the magnitude and phase angle of the voltage across the sense network 48 in accordance with the value obtained at blocks 266 and 268. At block 342 and 344 the microprocessor computes the magnitude of the impedance and the phase angle of the impedance of the body network from the values obtained at blocks 334, 336, 338 and 380 in accordance with equations (6) and (7). At block 346 the microprocessor 200 then calculates the resistance and reactance components of the body network in accordance with equations (8) and (9) from the magnitude and phase angle of the impedance calculated for the body network. At block 348 the microprocessor 200 then controls the display 12 to display the resistance value calculated for the body network at block 346. If the microprocessor determines at block 350 that the research mode is enabled, the microprocessor proceeds to block 352 to display the reactance value calculated for the body network.

The microprocessor implements a typical body fat algorithm depicted by the flow chart in FIG. 8. More particularly, this algorithm is used to determine the body fat percentage of a male in accordance with the following equation:

$$B.F.\% = 100[1-(0.2027W+0.3425H^2/R-0.0767A-+0.210H+4.9752-15.4919)/W] \quad \text{Eq. (10)}$$

Where W represents weight in kilograms; R represents the person's calculated resistance; A represents age in years and H represents the height of the person in centimeters. When implementing this algorithm, the microprocessor 200 at block 354 multiplies the weight input via the keyboard 14 for the person by 0.2027 and at block 356 saves this value as a partial sum. At block 358 the microprocessor squares the value of the person's height entered via the keyboard 14 and at block 360 multiplies the value calculated at block 358 by 0.3425. The product determined at block 360 is then divided by the resistance calculated for the body network at a block 362. Thereafter, the microprocessor adds the value calculated at block 362 to the partial sum saved at block 356. At block 366 the person's age is multiplied by 0.0767 and this value is then subtracted at block 368 from the partial sum calculated at block 364. At block 370, the microprocessor multiplies the person's height by 0.210 and adds this product at block 372 to the partial sum determined at block 368. At block 374 a constant of 4.9752 is added to the partial sum calculated at block 372 and at block 276, the person's constant 15.4919 is subtracted from the sum determined at block 374. At block 378 the partial sum calculated at block 376 is saved as the lean body mass. Thereafter, the lean body mass is divided by the person's weight at block 380. At block 382 the value calculated at block 380 is subtracted from 1 and at block 384 this value multiplied by 100 so as to determine at block 386 the percentage body fat of the person. A typical percentage body fat formula for a female is very similar to that given above for a man given above but is as follows:

$$100[1-(0.2027w+0.3425h^2/R-0.0767A+0.210h--15.4919)/w] \quad \text{Eq. (11)}$$

It is noted that equations (10) and (11) are representative of a number of the equations used to calculate body fat percentages for different people, the microprocessor selecting the appropriate equation for a given person based uponon the input data describing the person as discussed above.

The microprocessor 200 determines a person's ideal weight, IW in accordance with the following equation:

$$IW = \frac{\text{Lean Body Mass}}{\left(1 - \frac{\text{Ideal Body Fat \%}}{100}\right)} \quad \text{Eq. (12)}$$

The ideal body fat percentage for the person is selected from a table which stores values for both males and females in each of the following categories: elite, competitive and standard as discussed above. As further discussed above, the user can enter a user selected ideal body fat percentage value via the keyboard 14. As shown in FIG. 9, the microprocessor implements the ideal weight algorithm as follows. At a block 388 the microprocessor determines whether the user has entered an ideal body fat percentage value and if so, the microprocessor at block 390 sets the ideal body fat percentage equal to the user entered value. If the user has not entered an ideal body fat percentage, the microprocessor proceeds to block 392 to determine whether the values stored for the elite mode are to be used and if so, the microprocessor proceeds to block 394 to set the ideal body fat percentage equal to the elite value stored for a person of the given gender. For example, a value of 6.5% may be stored for a male and a value of 14.0% may be stored for a female in the elite mode. If the microprocessor determines at a block 396 that the competitive mode has been selected, the microprocessor proceeds from block 396 to block 398 to set the ideal body fat percentage equal to the value stored for the competitive mode for a person of the specified gender. For example, a value of 9.0% may be stored for a male and a value of 17.0% may be stored for a female in the competitive mode. If the microprocessor determines at block 396 that the ideal body fat percentage is to be calculated using a standard value, the microprocessor selects the standard value for a person of the specified gender. For example, a value of 14.5% may be stored for a male and a value of 21.5% may be stored for a female in the standard mode. It is noted that the ideal body fat percentage values for each mode may be stored in a table in the EEPROM so as to be updatable. Thereafter, the microprocessor 200 at a block 402 sets a term representing the ideal body fat fraction equal to the ideal body fat percentage, set at one of the blocks 390, 394, 398 or 400, divided by 100. Thereafter, the microprocessor at a block 404 sets a term representing the ideal lean body mass fraction equal to 1 minus the value calculated at block 402. Thereafter, the microprocessor determines the ideal weight of the person by dividing the lean body mass determined at block 378 by the ideal lean body mass fraction determined at block 404.

Figure 10A:
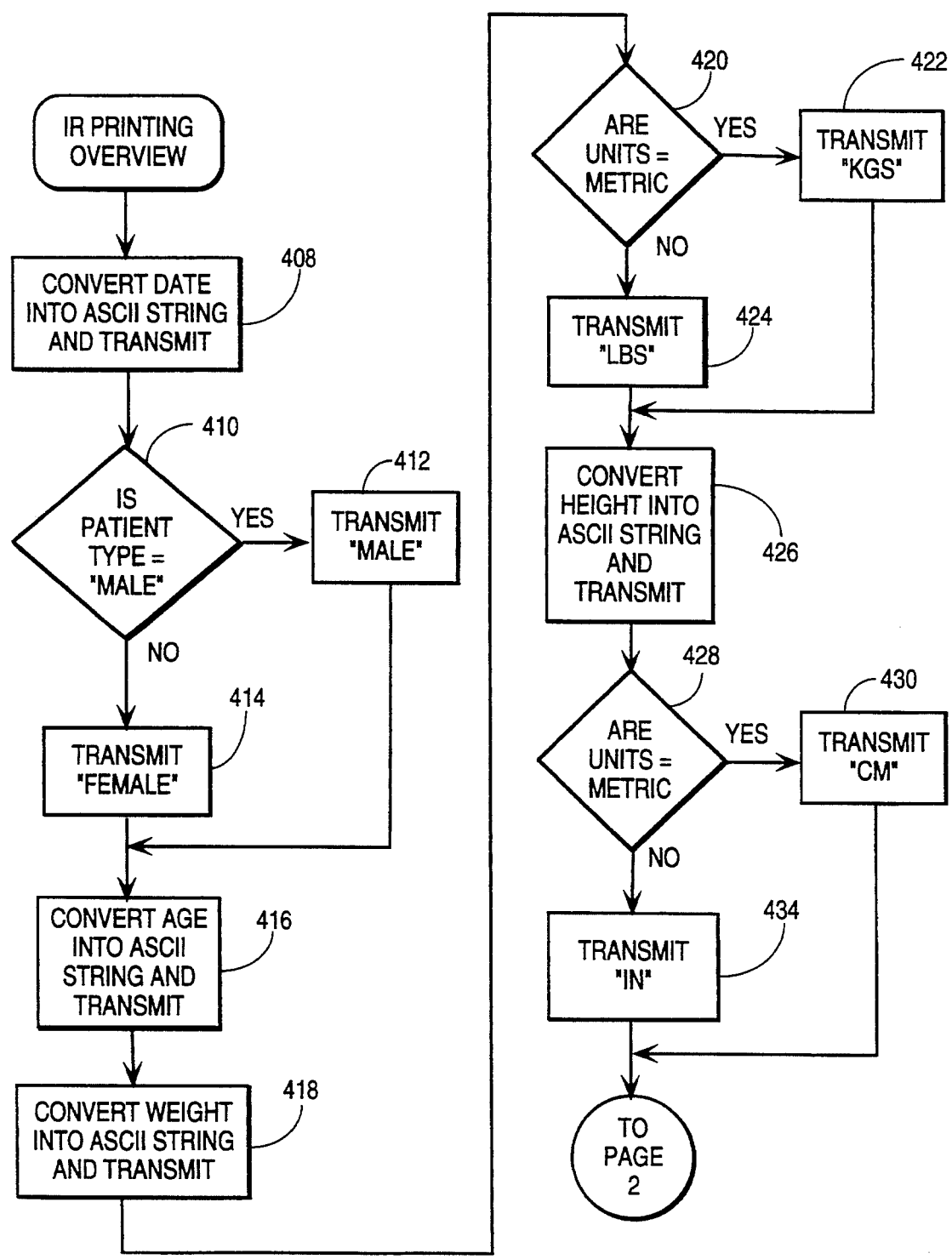
FIGS. 10A-10B form a flow chart illustrating an infrared communication routine.
Figure 10B:
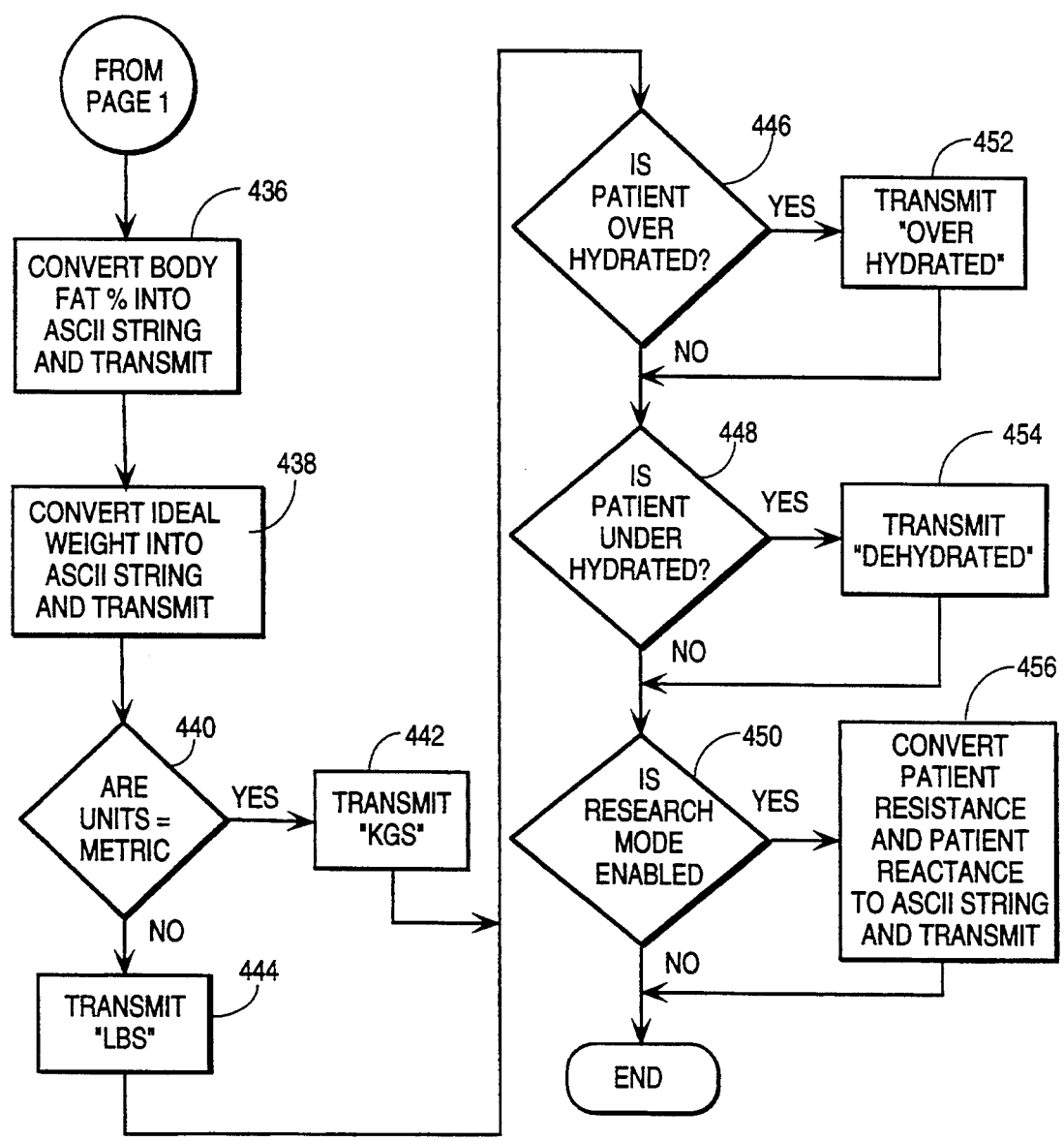
Figure 11:
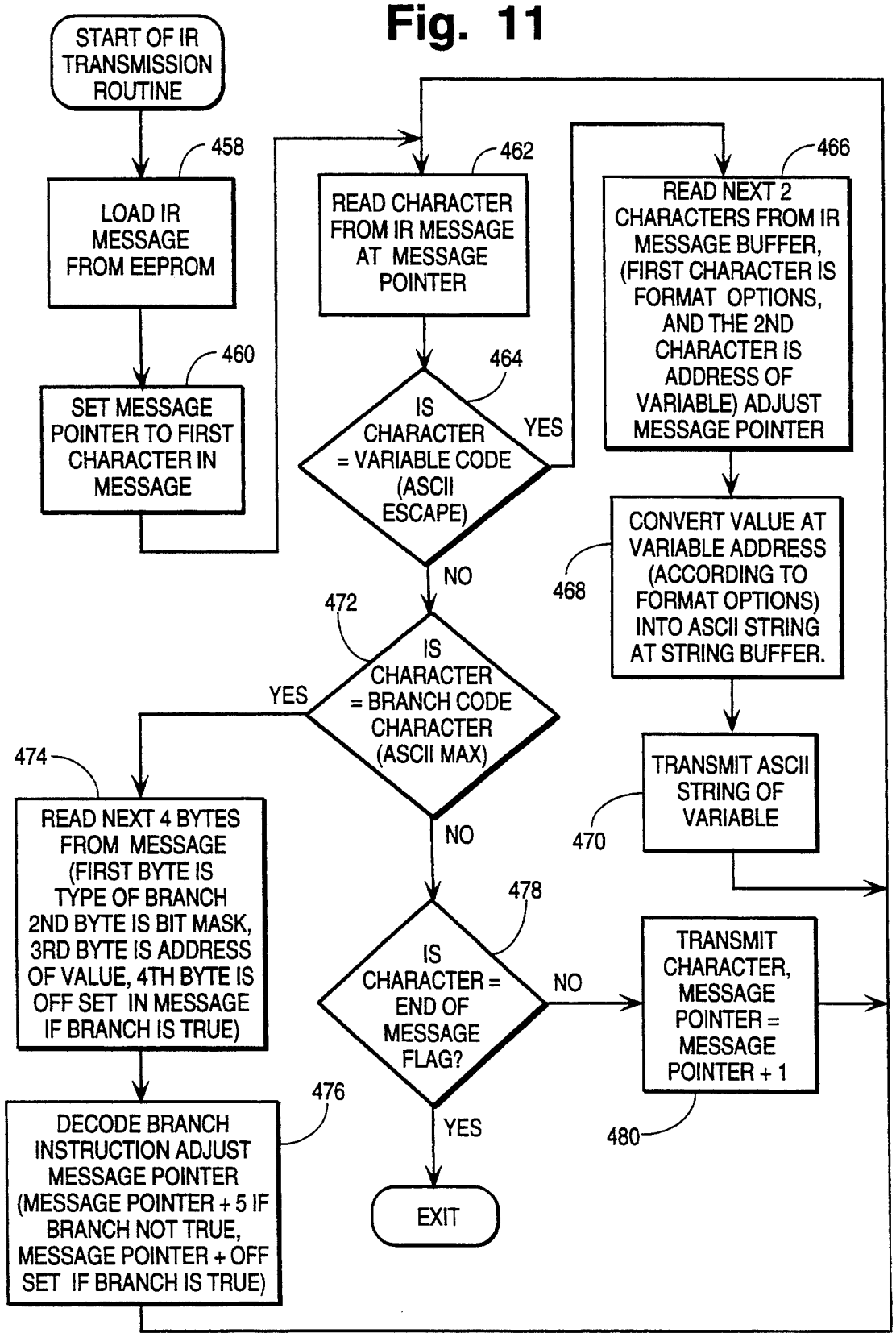
FIG. 11 is a flow chart illustrating an infrared transmission routine.

The microprocessor 200 operates in accordance with the flow charts depicted in FIGS. 10A-B and FIG. 11 to control the transmission of body composition data to a remote P.C. and/or printer capable of receiving such transmissions so that a hard copy of the information may be obtained. More particularly, at block 408 the microprocessor 200 converts the date information entered via the keyboard 14 into an ASCII string and calls the transmission routine to transmit the date information. Thereafter, at block 410 the microprocessor determines whether the person for whom the body composition data has been entered is a male or not. If so, the microprocessor proceeds to block 412 to transmit a message indicating "male". Otherwise, the microprocessor proceeds from block 410 to block 414 to transmit data representing "female". At block 416 the microprocessor 200 converts the stored age information into an ASCII string and transmits the age information for the person. At block 418 the microprocessor converts the weight information into an ASCII string and transmits the weight information. At block 420 the microprocessor determines whether the units are metric or not. If so, the microprocessor proceeds to block 422 to transmit the term "KGS"; otherwise, the microprocessor at block 424 transmits the term "lbs". At block 426 the microprocessor converts the height information for the person into an ASCII string and transmits the height information. If the microprocessor determines at block 428 that the units for the height information are metric units the microprocessor proceeds to block 430 to transmit "CM". Otherwise, the microprocessor transmits the English units for height as "IN". The microprocessor at block 436 converts the calculated body fat percentage into an ASCII string and transmits the data to the remote site. Thereafter, at block 438 the microprocessor converts the calculated ideal weight into an ASCII string and transmits the information. If the microprocessor determines at block 440 that the weight was calculated in metric units, the microprocessor proceeds to block 442 to transmit the term "KTS". Otherwise, the microprocessor at block 444 transmits the English units for the weight term as "LBS". At block 446 the microprocessor 200 determines whether the patient is over-hydrated or not, and if so the microprocessor proceeds to block 452 to transmit the term "over-hydrated". Similarly, the microprocessor determines at a block 448 whether the patient is under-hydrated and if so, the microprocessor proceeds to block 454 to transmit the term "dehydrated". It is noted that if the microprocessor determines that the patient is either over-hydrated or under-hydrated, the calculated impedance values and other terms dependent thereon may be inaccurate so that the over-hydration or under-hydration indication provides a warning regarding possible inaccuracies in the measurements. Thereafter, the microprocessor determines at block 450 whether the research mode is enabled or not. If the research mode is enabled, the microprocessor proceeds to block 456 to convert the patient's resistance and reactance values into an ASCII string and to transmit the information. If the research mode is not enabled, only the calculated resistance is transmitted.

As shown in FIG. 11, at the start of the infrared transmission routine, the microprocessor 200 at a block 458 loads the message to be transmitted from the EEPROM. Thereafter, the microprocessor at block 460 sets a message pointer to the first character in the message. At block 462 the microprocessor 200 reads the character to which the message pointer is pointing from the IR message. If the microprocessor 200 determines at block 464 that the character is a variable code such as an ASCII escape, the microprocessor proceeds to block 466. At block 466 the microprocessor reads the next two characters from the IR message buffer. The first character represents a format option whereas the second character represents the address of the variable. At block 466 the microprocessor 200 further adjusts the message pointer. Thereafter, at block 468 the microprocessor converts the value at the variable address indicated by the second character according to the format option indicated by the first character into an ASCII string at a string buffer. At block 470, the microprocessor transmits the ASCII string of the variable and returns to block 462. If the microprocessor determines at block 464 that the character is not a variable code, the microprocessor proceeds to block 472 to determine whether the character is a branch code character and if so the microprocessor proceeds to block 474. At block 474 the microprocessor reads the next four bytes from the message. The first byte represents the type of branch, the second byte represents the least significant bit mask, the third byte represents the address of the value and the fourth byte represents the offset in the message if the branch is true. Thereafter, at block 476 the microprocessor decodes the branch instruction and adjusts the message pointer. If the microprocessor determines at block 472 that the character is not a branch code the microprocessor proceeds to block 478 to determine whether the character is an end of message flag and if not, the microprocessor at block 480 transmits the character and increments the message pointer.

Many modifications and variations of the present invention are possible in light of the above teachings. Thus, it is to be understood that, within the scope of the appended claims, the invention may be practiced otherwise than as described hereinabove.

We claim:

1. A body composition analyzer comprising:
a plurality of electrodes attachable to the body of a person, said body forming a network of unknown impedance;
a reference network of known impedance coupled in series with said body network;
a source of substantially constant peak to peak alternating current coupled to at least one of said electrodes and to said reference network;
a voltage sensing circuit coupled to a pair of said body electrodes and to said reference network to provide a signal representative of the sensed voltage across said body network and a signal representative of the sensed voltage across said reference network;
digital processing means coupled to said voltage sensing circuit for calculating at least one value representative of said unknown body impedance from said known reference network impedance and a ratio of the sensed voltage across said body network and said sensed voltage across said reference network.

2. A body composition analyzer as recited in claim 1 further including means for multiplying each of said body voltage signal and said reference voltage signal by an in-phase signal and an out-of-phase signal shifted from said in-phase signal by ninety degrees to provide an in-phase body voltage signal, an out-of-phase body voltage signal, an in-phase reference voltage signal and an out-of-phase reference voltage signal coupled to said digital processing means.

3. A body composition analyzer as recited in claim 2 wherein said digital processing means includes means for calculating the magnitude of the voltage across said body network from said in-phase and out-of-phase body voltage signals and the magnitude of the voltage across said reference network from said in-phase and out-of-phase reference voltage signals and means for calculating the magnitude of said unknown impedance from the magnitude of the known impedance of said reference network and the ratio of the magnitude of the voltage across said body network and the magnitude of the voltage across said reference network.

4. A body composition analyzer as recited in claim 3 wherein said digital processing means includes means for calculating the phase angle of the voltage across said body network from said in-phase and out-of-phase body voltage signals and the phase angle of the voltage across said reference network from said in-phase and out-of-phase reference voltage signals and means for calculating the phase angle of the unknown body impedance from the ratio of the phase angle of the voltage across said body network and the phase angle of the voltage across said reference network.

5. A body composition analyzer as recited in claim 4 wherein said body impedance phase angle calculating means calculates said ratio of the phase angle of the voltage across said body network and the phase angle of the voltage across said reference network from the difference between the phase angles of the voltage across the body network and the voltage across the reference network.

6. A body composition analyzer as recited in claim 4 wherein said digital processing means includes means for calculating the resistance of the body from the calculated magnitude and phase angle of the body impedance.

7. A body composition analyzer as recited in claim 6 further including means for displaying said body resistance.

8. A body composition analyzer as recited in claim 6 further including input means for entering the weight, height, age and gender of said person, said digital processing means including means responsive to said person's gender for determining a value representative of the person's body fat from said calculated resistance, weight, height and age.

9. A body composition analyzer as recited in claim 8 wherein said digital processing means includes means for storing in a nonvolatile programmable memory a plurality of body fat algorithms for calculating said value representative of body fat and means responsive to the person's entered gender to select the body fat algorithm according to which the person's body fat value is to be calculated.

10. A body composition analyzer as recited in claim 9 wherein said algorithm selecting means is responsive to the person's age to select said body fat algorithm.

11. A body composition analyzer as recited in claim 9 wherein said input means allows a person to enter his ethnicity and said algorithm selecting means is responsive to the person's ethnicity to select said body fat algorithm.

12. A body composition analyzer as recited in claim 8 wherein said digital processing means includes means for storing in a nonvolatile programmable memory at least one body fat algorithm for calculating said value representative of body fat and a plurality of selectable constants for use in said algorithm and means for selecting at least one constant to be used in said algorithm from said plurality of stored constants in response to at least one of the entered characteristics of said person.

13. A body composition analyzer as recited in claim 12 wherein said entered characteristic to which said selecting means is responsive is gender.

14. A body composition analyzer as recited in claim 12 wherein said entered characteristic to which said selecting means is responsive is age.

15. A body composition analyzer as recited in claim 12 wherein said entered characteristic to which said selecting means is responsive is ethnicity.

16. A body composition analyzer as recited in claim 8 further includes means for storing a plurality of values representing ideal body fat percentages each of which is selectable by a user via said input means and wherein said digital processing means further includes means for calculating a person's lean body mass from said person's weight, height, age and calculated resistance and means for calculating a value representing the person's ideal body weight from said person's calculated lean body mass and ideal body fat percentages.

17. A body composition analyzer as recited in claim 8 wherein said input means allows a user to enter a body fat percentage value and said digital processing means further includes means for calculating a value representing the person's ideal body fat from said person's weight, height and age and said entered body fat percentage value.

18. A body composition analyzer as recited in claim 4 wherein said digital processing means includes means for calculating the reactance of the body from the calculated magnitude and phase angle of the body impedance.

19. A body composition analyzer as recited in claim 6 further including means for displaying said body reactance.

20. A body composition analyzer as recited in claim 1 further including means for calculating the resistance and reactance of the body from said calculated body impedance and means for displaying said resistance and said reactance.

21. A body composition analyzer as recited in claim 1 further including input means for entering the weight, height, age and gender of said person, said digital processing means including means for calculating a value representative of the person's body fat from said calculated resistance, weight, height and age.

22. A body composition analyzer as recited in claim 21 wherein said digital processing means includes means for storing in a nonvolatile programmable memory a plurality of body fat algorithms for calculating said value representative of body fat and means responsive to the entered gender to select the body fat algorithm according to which a person's body fat value is to be calculated.

23. A body composition analyzer as recited in claim 22 wherein said algorithm selecting means is responsive to the person's age to select said body fat algorithm.

24. A body composition analyzer as recited in claim 22 wherein said input means allows a person to enter his ethnicity and said algorithm selecting means is responsive to the person's ethnicity to select said body fat algorithm.

25. A body composition analyzer as recited in claim 21 wherein said digital processing means includes means for storing in a nonvolatile programmable memory at least one body fat algorithm for calculating said value representative of body fat and a plurality of selectable constants for use in said algorithm and means for selecting one or more constants to be used in said algorithm from said plurality of stored constants in response to at least one of the entered characteristics of said person.

26. A body composition analyzer as recited in claim 25 wherein said entered characteristic to which said selecting means is responsive is gender.

27. A body composition analyzer as recited in claim 26 wherein said entered characteristic to which said selecting means is responsive is age.

28. A body composition analyzer as recited in claim 26 wherein said entered characteristic to which said selecting means is responsive is ethnicity.

29. A body composition analyzer as recited in claim 21 further includes means for storing a plurality of values representing ideal body fat percentages each of which is selectable by a user via said input means and wherein said digital processing means further includes means for calculating a person's lean body mass from said person's weight, height, age and calculated resistance and means for calculating a value representing the person's ideal body weight from said person's calculated lean body mass and ideal body fat percentages.

30. A body composition analyzer as recited in claim 21 wherein said input means allows a user to enter a body fat percentage value and said digital processing means further includes means for calculating a value representing the person's ideal body fat from said person's weight, height and age and said entered body fat percentage value.

31. A body composition analyzer as recited in claim 21 wherein said digital processing means includes means for storing in a nonvolatile programmable memory at least one body fat algorithm software routine and a plurality of mathematical operation software routines called by said body fat algorithm, wherein said memory may be programmed to update said body fat algorithm without requiring said mathematical operation software routines to be changed.

32. A body composition analyzer as recited in claim 1 further including means for determining the existence of a condition indicating the possibility of inaccurate impedance measurements and means for providing an indication of a possible error.

33. A body composition analyzer as recited in claim 32 including a load network connectable in series with said reference network and having a measurable impedance, said load network being coupled to said voltage sensing circuit to provide a signal representative of the sensed voltage across the load network, said digital processing means calculating at least one value representative of the impedance of said load network from said known reference network impedance and a ratio of the sensed voltage across said load network and said sensed voltage across said reference network and including means for comparing said load network impedance value to a predetermined value to determine a condition indicating the possibility of inaccurate impedance measurements.

34. A body composition analyzer as recited in claim 33 wherein said load network includes a high resistance component and a low reactance component.

35. A body composition analyzer as recited in claim 33 wherein said load network includes a high reactance component and a low resistance component.

36. A body composition analyzer as recited in claim 32 including means for detecting a faulty connection of one of said electrodes to a person's body.

37. A body composition analyzer as recited in claim 1 including wireless communication means for transmitting calculated impedance data to a remote unit for printing.

38. A body composition analyzer comprising:
a hand-held housing;
a keyboard mounted on said housing for inputting data representing a plurality of characteristics of the person whose body composition is to be analyzed;
a plurality of electrodes connectable to a person's body;
measurement circuitry contained in said housing and coupled to said electrodes for generating an alternating signal applied to at least one of said electrodes and for sensing a voltage across a pair of said electrodes to provide a digital signal representative thereof;
a load network connectable to said alternating signal for producing a measurable voltage;
a microprocessor control contained in said housing responsive to said input data and said digital signal representing the voltage across said electrodes for calculating a plurality of body composition values, said microprocessor control including means for sensing the voltage across said load network and comparing a value responsive to said load network voltage to a predetermined value to detect the existence of at least one condition that can affect the accuracy of said calculated body composition values; and means responsive to said microprocessor control determining the existence of said condition for providing an indication to a user that a possible error has occurred.

39. A body composition analyzer as recited in claim 38 wherein said indication is visual.

40. A body composition analyzer as recited in claim 38 wherein said indication is audible.

41. A body composition analyzer as recited in claim 38 wherein said compared value represents the impedance across said load voltage network.

42. A body composition analyzer as recited in claim 41 wherein said load network includes a high resistance component and a low reactance component.

43. A body composition analyzer as recited in claim 41 wherein said load network includes a high reactance component and a low resistance component.

44. A body composition analyzer, comprising:
a housing;
a keyboard mounted on said housing providing means for inputting data representing a plurality of characteristics of the person whose body composition is to be analyzed, said inputtable characteristics including gender;
a plurality of electrodes connectable to a person's body;
measurement circuitry contained in said housing and coupled to said electrodes providing means for generating an alternating signal applied to at least one of said electrodes and for sensing a voltage across a pair of said electrodes to provide a digital signal representative thereof;
a memory device contained in said housing providing means for storing a plurality of algorithms for male users and storing a plurality of algorithms for female users; and
a microprocessor control contained in said housing providing means for controlling said measurement circuitry, selecting one of said algorithms based on input data representing a person's gender and at least one other body type characteristic, and responsive to said input data and said digital signal representing the voltage across said electrodes for calculating a body composition value in accordance with said selected algorithm.

45. A body composition analyzer as recited in claim 44, wherein said housing is a hand-held housing.

46. A body composition analyzer as recited in claim 45, further comprising a display mounted on said housing for simultaneously displaying said input data and said body composition values.

47. A body composition analyzer as recited in claim 45 wherein said microprocessor control selects one of said algorithms based on input data representing a person's gender and fitness level.

48. A body composition analyzer as recited in claim 45 wherein said microprocessor control selects one of said algorithms based on input data representing a person's gender and age.

49. A body composition analyzer as recited in claim 45 wherein said microprocessor control selects one of said algorithms based on input data representing a person's gender and ethnicity.

50. A body composition analyzer as recited in claim 45 further including a wireless communication device mounted in said housing for transmitting input data and calculated body composition data to a peripheral device.

51. A body composition analyzer as recited in claim 45 wherein said microprocessor control calculates a body composition value representing the resistance components of said body's impedance and a reactance component of said body's impedance.

52. A body composition analyzer as recited in claim 45 wherein said microprocessor control calculates a body composition value representing body fat.

53. A body composition analyzer as recited in claim 45 wherein said microprocessor control calculates a body composition value representing ideal weight.

54. A body composition analyzer as recited in claim 53 wherein said microprocessor control stores a plurality of predetermined values used to calculate ideal weight, each value being associated with a person of a particular gender and physical fitness, each of said predetermined values being selectable by a user actuating said keyboard and said microprocessor control calculating the ideal weight of the person based upon at least one other of said calculated body composition values and said predetermined value selected by said user for said ideal weight calculation.

55. A body composition analyzer as recited in claim 54 wherein said microprocessor control is responsive to at least one other of said calculated body composition values and an ideal body fat value input to said analyzer via said keyboard for calculating said ideal weight value.

56. A body composition analyzer as recited in claim 45 further comprising a programmable memory for allowing said body composition analyzer to be updated.

57. A body composition analyzer as recited in claim 56 wherein said programmable memory stores a plurality of constants for use in said algorithms such that said constants are updatable.

58. A body composition analyzer as recited in claim 57 wherein said microprocessor control includes mathematical subroutines callable by said algorithms, said mathematical subroutines being stored separately from said body composition value calculating algorithms to allow said algorithms to be replaced without requiring that said mathematical subroutines be replaced.

* * * * *